(12) United States Patent
Emil et al.

(10) Patent No.: US 11,859,649 B2
(45) Date of Patent: Jan. 2, 2024

(54) BEARING ASSEMBLIES FOR SELECTIVELY COUPLING COMPONENTS

(71) Applicant: Medos International Sarl, Le Locle (CH)

(72) Inventors: Cory Emil, Milton, MA (US); Eric Biester, Barrington, RI (US); Joshua Rodriguez, Raynham, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 349 days.

(21) Appl. No.: 17/346,168

(22) Filed: Jun. 11, 2021

(65) Prior Publication Data

US 2022/0397154 A1 Dec. 15, 2022

(51) Int. Cl.
*F16B 21/16* (2006.01)
*A61B 17/00* (2006.01)

(52) U.S. Cl.
CPC .. *F16B 21/165* (2013.01); *A61B 2017/00464* (2013.01); *Y10T 403/592* (2015.01)

(58) Field of Classification Search
CPC .. A61B 2017/0046; A61B 2017/00464; A61B 2017/00477; A61B 2017/00486; F16B 2/16; F16B 7/1409; F16B 21/165; Y10S 403/06; Y10T 403/32475; Y10T 403/592
USPC .............. 403/109.2, 322.2, DIG. 6
See application file for complete search history.

(56) References Cited

U.S. PATENT DOCUMENTS

| | | | |
|---|---|---|---|
| 4,082,342 A * | 4/1978 | Ailshie | F16B 21/165 292/144 |
| 4,656,698 A * | 4/1987 | Arakawa | F16B 2/16 24/115 L |
| 4,938,622 A * | 7/1990 | Stoerzbach | F16B 21/165 403/380 |
| 5,505,737 A * | 4/1996 | Gosselin | A61B 17/32002 279/75 |
| 5,692,851 A * | 12/1997 | Pace | F16B 21/165 403/322.2 |

(Continued)

FOREIGN PATENT DOCUMENTS

EP 2713061 A1 * 4/2014 ............ F16B 21/165

OTHER PUBLICATIONS

DePuy Synthes Spine. A Solution for Simple and Complex Spine Pathology MATRIX Spine System—Degenerative. Surgical Technique Guide. 2017.

*Primary Examiner* — Josh Skroupa
(74) *Attorney, Agent, or Firm* — Barnes & Thornburg LLP

(57) ABSTRACT

Bearing assemblies for selectively coupling to surgical instruments A bearing assembly can include a housing with a cavity, a first race in the cavity that translates but does not rotate relative to the housing, bearing elements disposed in the first race that move radially in and out of a central passage of the first race, and a second race that is fixed in the cavity. The first race can be biased toward an opening of the cavity, the second race can surround the first race with an inner surface having a tapered diameter configured to contact the bearing elements as the first race moves distally relative to the second race and urge the plurality of bearing elements radially inward to selectively lock the bearing assembly to a surgical instrument disposed within the central passage of the first race.

34 Claims, 19 Drawing Sheets

(56) References Cited

U.S. PATENT DOCUMENTS

| | | | | |
|---|---|---|---|---|
| 6,511,100 | B1* | 1/2003 | Le Clinche | F16L 37/23 |
| | | | | 403/322.2 |
| 7,331,813 | B2* | 2/2008 | Tsujita | F16B 21/165 |
| | | | | 439/348 |
| 7,963,717 | B2* | 6/2011 | Seger | F16B 21/165 |
| | | | | 403/322.2 |
| 8,251,606 | B2* | 8/2012 | Blanchard | F16B 21/165 |
| | | | | 403/322.2 |
| 8,800,999 | B2* | 8/2014 | Puzio | B25B 23/0035 |
| | | | | 279/75 |
| 8,960,734 | B2* | 2/2015 | Camp | E05B 1/0038 |
| | | | | 292/228 |
| 10,995,890 | B2* | 5/2021 | Hafele | F16L 37/23 |
| 11,529,180 | B2* | 12/2022 | Russell | A61B 17/162 |
| 11,576,685 | B2* | 2/2023 | Card | A61B 17/1703 |
| 2021/0179281 | A1* | 6/2021 | Kruts | F16B 21/165 |

* cited by examiner

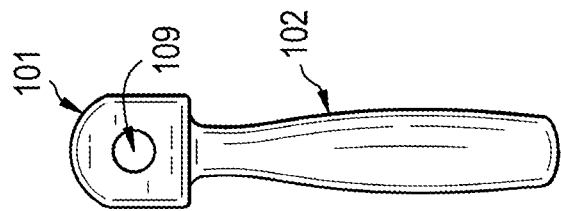
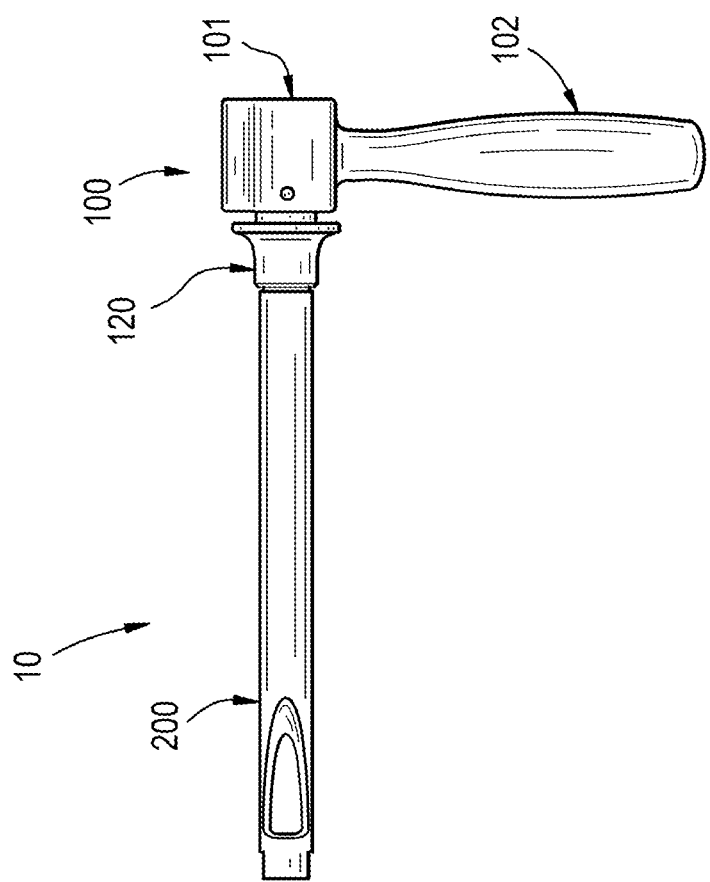
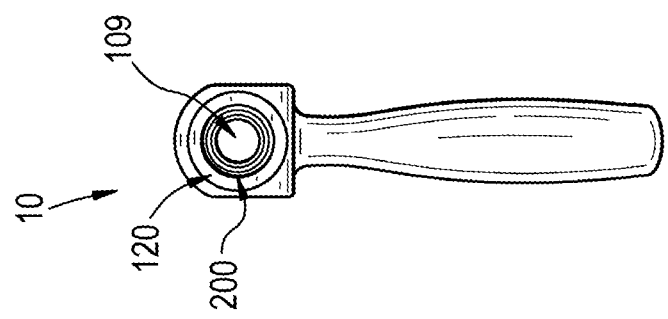

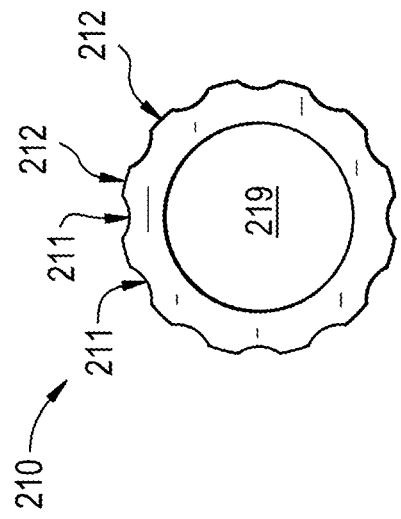
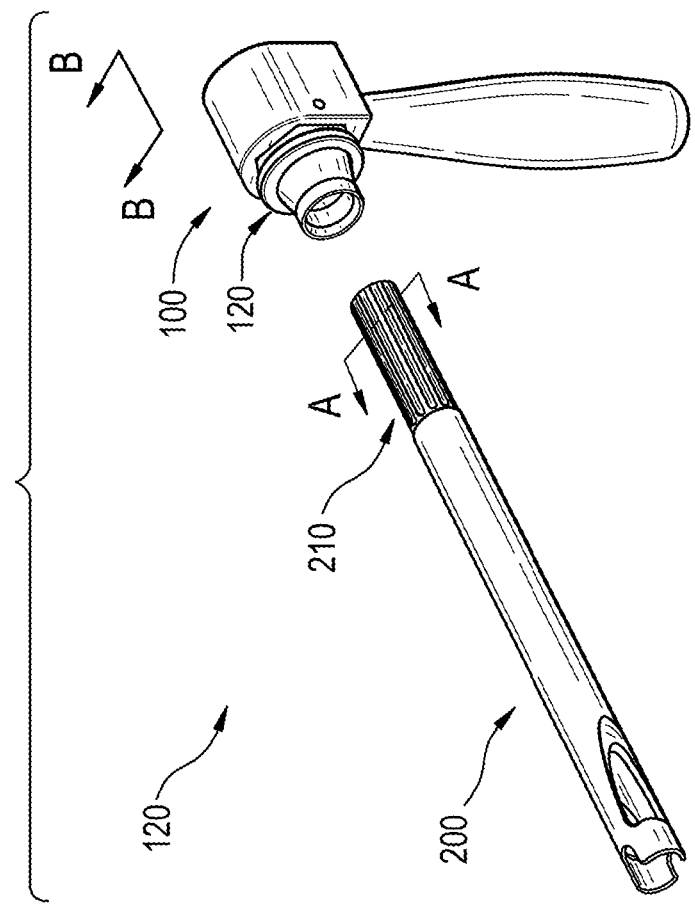

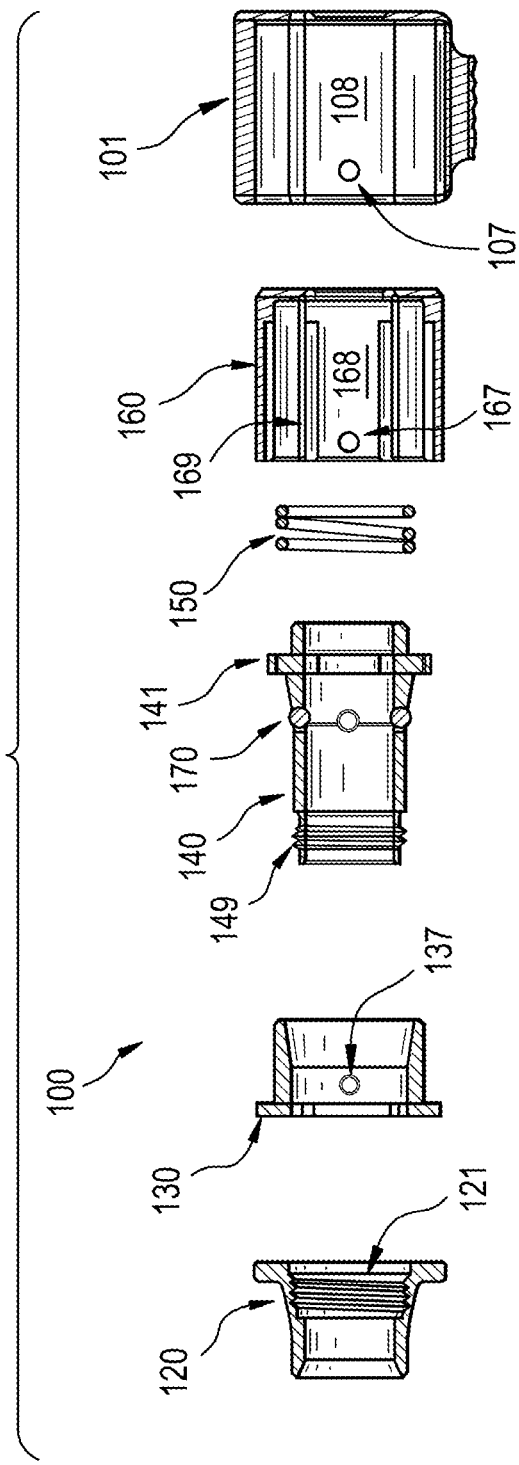

C-C

D-D

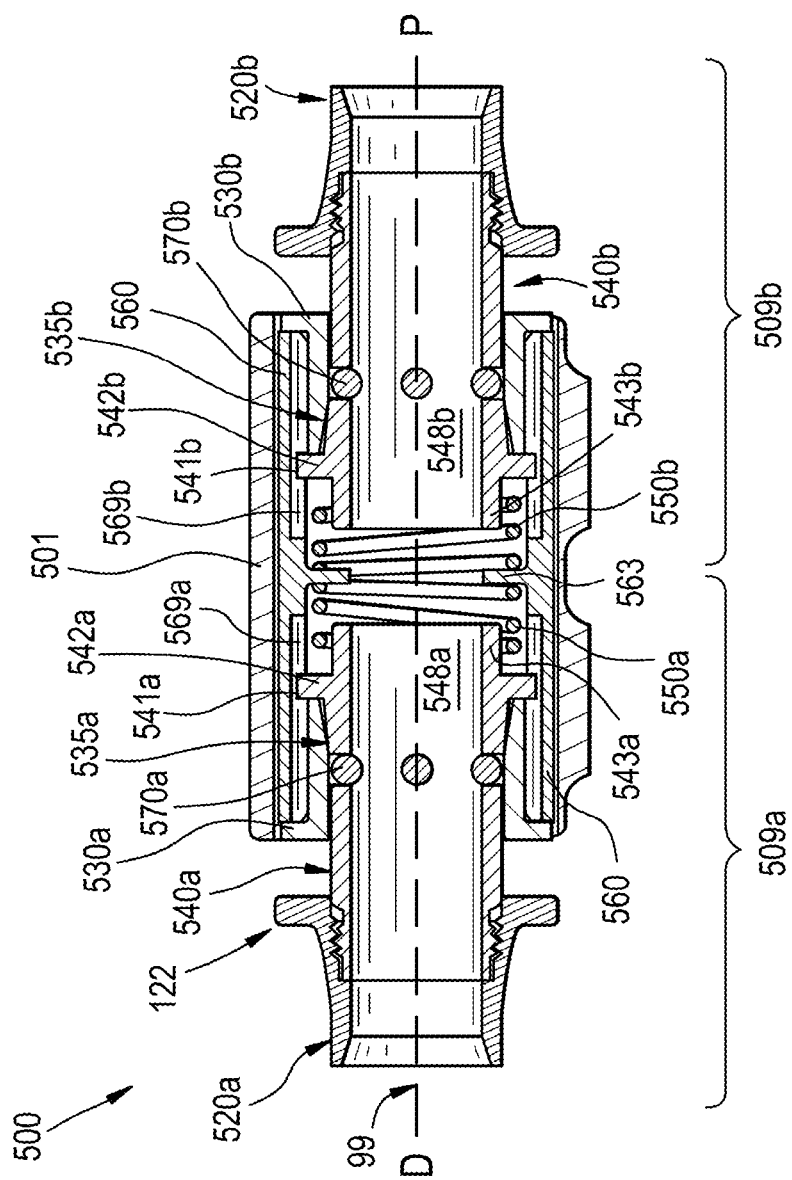

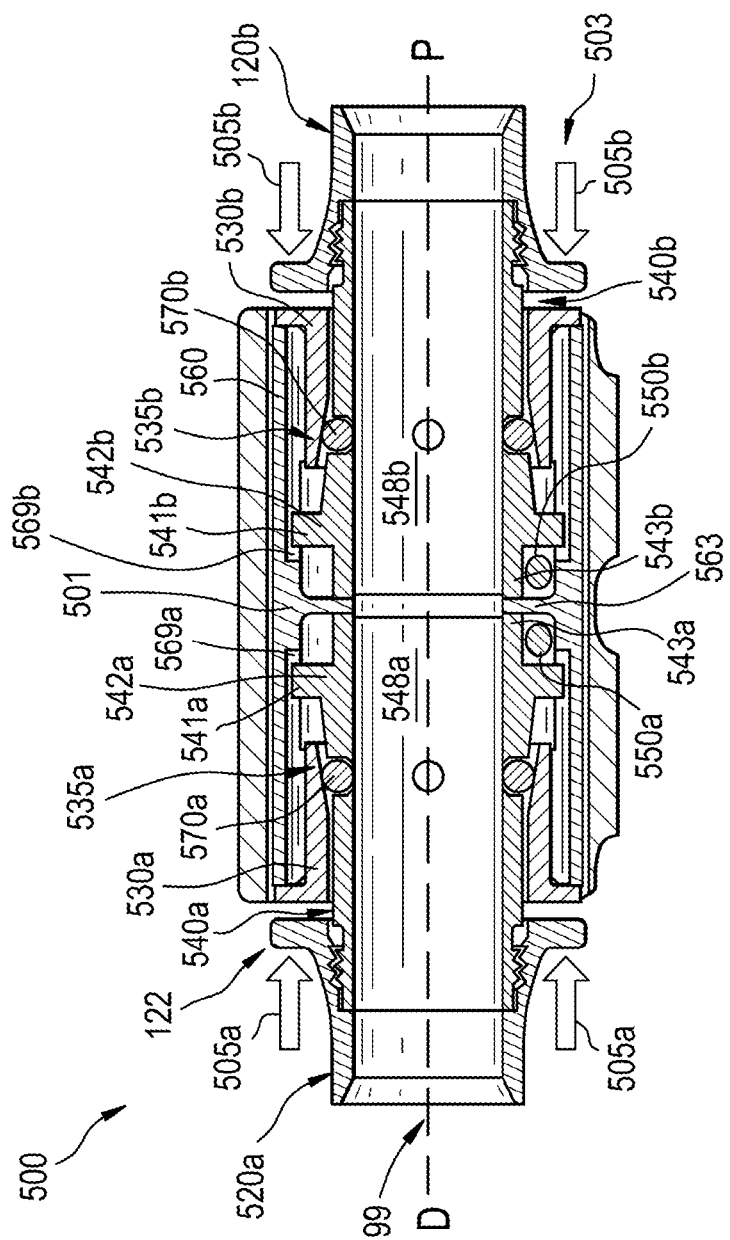

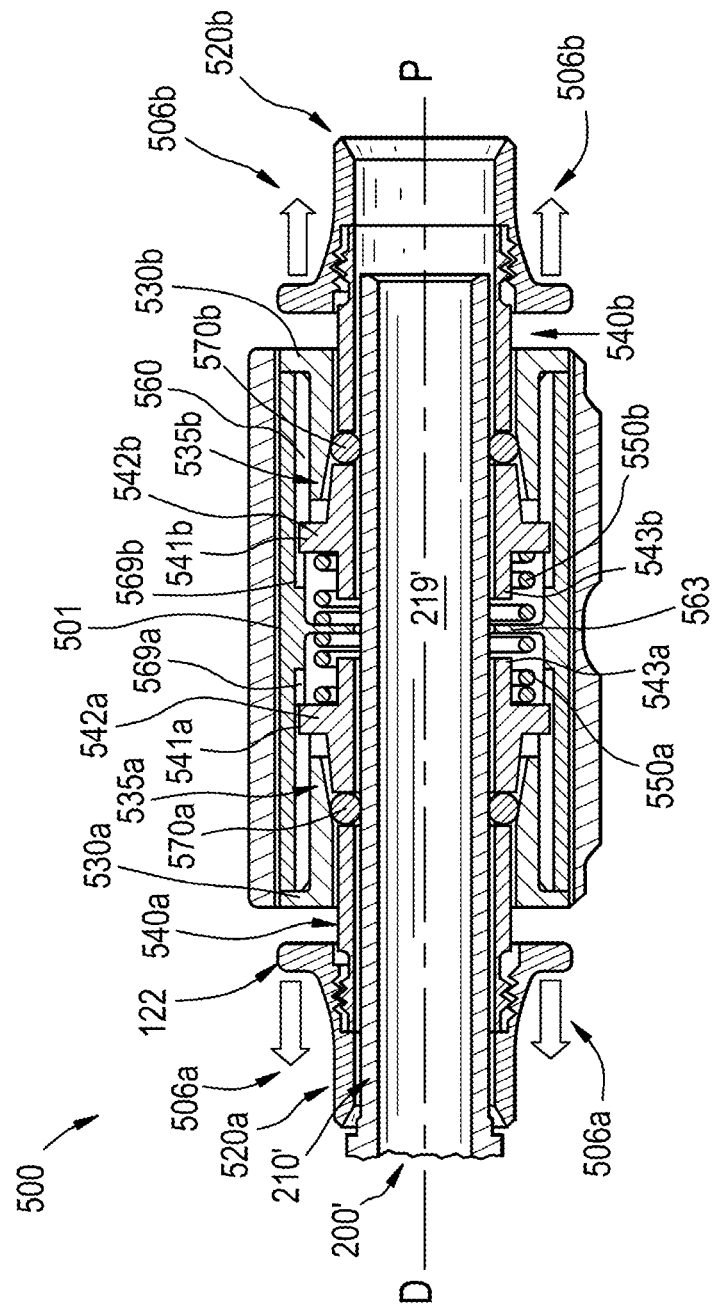

BEARING ASSEMBLIES FOR SELECTIVELY COUPLING COMPONENTS

FIELD

This disclosure relates generally to surgical instruments, systems, and methods, and more particularly to devices, systems, and methods for coupling components, such as an alignment guide and a handle, utilizing a bearing assembly that provides for application of axial and radial forces between the components.

BACKGROUND

In many types of surgery, including spine surgery, modular handles are commonly used to deliver torque to an implant, instrument, or other component, and then subsequently removed for cleaning or to be assembled to another component. One such example involves a modular handle which can be assembled to a set screw alignment guide for providing counter-torque when tightening a set screw. During a typical procedure involving pedicle screw fixation, for example, a screwdriver with a torque-limiting handle attached thereto can be inserted through an alignment guide and used to lock a set screw with a pre-determined amount of torque. In order to prevent the load from being transmitted directly through the instrument into the patient's anatomy, the surgeon can apply torque in the reverse direction using a modular handle attached to the alignment guide. Typically, modular handles contain mechanisms that deliver torque by way of keyed flats on the handle and alignment guide, and they provide axial retention through an interference fit between a groove, hole, or slot on the alignment guide and a button, pin, or ball bearing(s) on the handle.

There is a need for a self-aligning modular handle which can be passively assembled in-situ, provide axial retention to prevent accidental disassembly, and deliver torque to an instrument. Additionally, there is a need for a device that can be easily oriented by the surgeon in a position that avoids tissue and boney anatomy as well as other instrumentation in the surgical field without having to remove the handle for readjustment. Accordingly, there is a need for improved systems, methods, and devices for coupling components, such as a modular handle and other surgical instrument, in a manner that allows for selective application of axial and radial forces therebetween, as well as adjustment of relative positioning without the need for separating the two components.

SUMMARY

The present disclosure provides surgical instruments, systems, and methods for coupling components, such as an alignment guide and a handle, utilizing bearing assemblies that provide for application of axial and radial forces between the components. The bearing assemblies disclosed herein can be utilized in a variety of applications to provide selective coupling between surgical instruments in a manner that can be easy to assemble, can resist unintentional disassembly, can allow for imparting of torque/counter-torque forces between the components, can allow for easy re-positioning of components without requiring disassembly to do so, and can allow for complete disassembly when desired. One particular application of the embodiments disclosed herein can be in connection with modular handle assemblies that are often utilized in surgical procedures to impart torque/counter-torque forces onto another instrument or component. In such an application, it can be desirable for a modular handle assembly to be easily coupled with another component and locked such that it can be utilized to impart torque thereto, but also easily unlocked for repositioning or disassembly.

Certain aspects of the present disclosure provide a combined one-way axial and radial bearing mechanism, which consists of a set of ball bearings captured within dedicated pockets of an inner race. In some embodiments, an alignment guide is passed through the inner race which compresses a spring allowing the ball bearings to move radially outward as the handle slides on. In some embodiments, no active actuation is required to assemble the handle to the alignment guide, which can easily slide in one direction allowing the user to position the handle anywhere along the axis of the alignment guide. If the user attempts to slide the handle off the alignment guide in the other direction, the ball bearings are wedged between the alignment guide and a ramp within an outer race, thereby preventing the handle from being accidentally removed from the alignment guide. The handle can be retained the moment the ball bearings first contact the alignment guide and does not require that the ball bearings travel any distance to engage a groove, hole, or slot in the alignment guide. To disassemble the device (e.g., remove the alignment guide from the combined one-way axial and radial bearing mechanism), a user simply pulls back on an endcap coupled to the inner race, thereby releasing the ball bearings and allowing the device to slide off the end of the alignment guide.

A variety of different alignment guide designs are suitable for use with aspects of the present disclosure. For example, a proximal portion of the alignment guide can contain a set of longitudinal grooves running along the axis of the alignment guide instrument with which the ball bearings in the handle engage. An interference fit between the ball bearings and the groove is established by the movement of the inner race with respect to the outer race, which allows the combined one-way axial and radial bearing mechanism to deliver torque to the alignment guide instrument. When the combined one-way axial and radial bearing mechanism is first coupled with the alignment guide and rotated, the ball bearings will fall into the nearest groove, if not disposed in a groove already, making the device self-aligning. With the ball bearings trapped within the longitudinal grooves of the alignment guide and wedged by the ramp in the outer race, the device is dual-retaining, preventing both relative axial and rotational motion between the alignment guide and the device. When the user pulls back on the endcap, the ball bearings are released from the longitudinal grooves and the device is free to rotate about the axis of the alignment guide. When the endcap is released, the inner race is urged distally and the ball bearings fall back into the next nearest groove allowing the user to easily reposition the handle without removing it. As an added benefit, the mechanism has virtually no toggle when the ball bearings are engaged, making the device well-suited to alternative applications involving navigation (e.g., where rigid coupling is needed between a navigation array and instrument it is being utilized to track in a surgical theater). In addition, some embodiments have an inner flange of the handle in direct contact with the end of the alignment guide making the device impactable, with the load path avoiding the ball bearings completely.

Another embodiment includes a device having two opposed inner races moving in similar opposed outer races, with each inner and outer race set having the ball bearing mechanisms described above, aligned axially, but flipped 180° relative to each other. Such a configuration allows the device to retain an alignment guide and prevent motion along the axis of the alignment guide in both directions. Accordingly, squeezing corresponding and oppositely disposed endcaps together urges both the inner races towards each other and away from their respective outer races, thereby freeing the ball bearings and enabling the device to be continuously repositioned anywhere along the alignment guide until the endcaps are released and the position of the is locked about the alignment guide.

In one aspect, an assembly according to the present disclosure can include a housing defining a cavity with a central axis extending from a proximal end of the housing to a distal end of the housing, as well as an opening to the cavity formed at the distal end of the housing. The assembly can further include an inner race disposed in the cavity of the housing and defining an interface between the housing and the inner race, the interface enabling translation of the inner race along the central axis and resisting rotation of the inner race about the central axis, the inner race comprising an inner surface defining a central passage configured to receive a portion of an alignment guide. The assembly can also include a biasing element that urges the inner race distally along the central axis toward the opening. The assembly can further include an outer race disposed in the cavity and fixed relative to the housing, the outer race including an inner surface surrounding an outer surface of the inner race, at least a portion of the inner surface defining a tapered region having decreasing diameter towards the opening to the cavity. The assembly can also include a plurality of clamping elements carried by the inner race such that (i) movement of the inner race distally toward the opening of the cavity engages the plurality of clamping elements against the inner surface of the outer race, the inner surface of the outer race urging the plurality of clamping elements into the central passage of the inner race and towards the central axis, and (ii) movement of the inner race proximally away from the opening of the cavity translates the plurality of clamping elements along the tapered region such that the increasing diameter allows the plurality of clamping elements to move out of the central passage and away from the central axis. Further, after insertion of an alignment guide sized to contact the plurality of clamping elements into the central passage of the inner race in the proximal direction, engagement of the plurality of clamping elements with the tapered region prevents movement of the inner race and the alignment guide in the distal direction.

The various aspects and embodiments disclosed herein can include any of a variety of additional or alternative features or steps, all of which are considered within the scope of the present disclosure. For example, in one embodiment insertion of an alignment guide sized to contact the plurality of clamping elements into the central passage of the inner race in the proximal direction can cause the inner race to be translated proximally with the alignment guide until the clamping elements are allowed to move sufficiently out of the central passage to allow the alignment guide to pass further into the central passage and the cavity.

In another embodiment, the inner race can be moveable in the proximal direction to an unclamped position where the plurality of clamping elements are allowed to move away from the central axis to permit insertion of an alignment guide sized to contact the plurality of clamping elements into the central passage of the inner race in the proximal direction. Further, the inner race can be moveable in the distal direction to a clamped position wherein the plurality of clamping elements are urged towards the central axis to apply a clamping force to the alignment guide.

In another embodiment, the central passage of the inner race can be cylindrical, the plurality of clamping elements can be circumferentially fixed with respect to the inner race, and insertion of a cylindrical alignment guide comprising one or more grooves sized to receive and contact the plurality of clamping elements can cause the cylindrical alignment guide to be rotationally fixed about the central axis with respect to the housing.

In some embodiments, when an alignment guide is disposed in the central passage such that the plurality of clamping elements prevent movement of the alignment guide in the distal direction, translation of the inner race in the proximal direction can enable removal of the alignment guide in the distal direction.

In other embodiments, an end cap can be coupled to the inner race and extend out of the opening in the housing, the end cap defining a flange for applying a force to the inner race in the proximal direction to release an alignment guide.

In some embodiments, the biasing element can be a compression spring.

In some embodiments, the housing can include an insert disposed in an outer cavity of the housing, the insert defining the cavity containing the inner race to be inserted through the opening of the housing, and the insert defining an inner cavity. In some embodiments, the outer cavity can define a non-circular cross section parallel to the central axis, and an exterior of the insert can be configured to interface with the outer cavity such that the insert is rotationally fixed in the outer cavity about the central axis.

In some embodiments, the cavity can include a plurality of grooves extending parallel to the central axis, and the interface of the inner race can include a plurality of protrusions, each of the plurality of protrusions being translatably disposed in a corresponding one of the plurality of protrusions.

In some embodiments, the housing can define a stop surface in the cavity positioned to be contacted by an end of an alignment guide such that the stop surface defines a position of maximum insertion of the alignment guide in the cavity, and the stop can enable an impact force to be directed from the housing to an end of a fully inserted alignment guide via the stop.

In some embodiments, the housing can define a second opening into the cavity formed at the proximal end of the housing, the second opening being arranged such that an inner lumen of an alignment guide disposed in the central cavity of the inner race is accessible through the second opening.

In certain embodiments, the outer race can be rotationally fixed in the cavity about the central axis.

In some embodiments, the outer race can be configured to abut the inner race when the inner race is biased distally to a fully extended position. In the fully extended position, the plurality of clamping members can be urged toward a maximally inward position with respect to the central axis. Further, the inner race can be configured to abut the housing when the inner race is moved proximally to a fully compressed position, and, in the fully compressed position, the plurality of clamping elements can be free to move to a maximally outward position with respect to the central axis.

In some embodiments, the assembly can further include a handle coupled to the housing, the handle configured to enable a user to apply torque to the housing, the torque being transferred to an alignment guide disposed in the central passage via the interface of the inner race and the plurality of clamping elements.

In some embodiments, the housing can further include a second opening to the cavity formed at the proximal end of the housing, as well as a second inner race disposed in the cavity of the housing and translatable in the cavity along the central axis, the second inner race comprising a second inner surface defining a second central passage concentrically aligned with the central passage and configured to receive the portion of an alignment guide after passing through the central passage of the inner race. The assembly can further include a second outer race disposed in the cavity and fixed along the central axis, the second outer race comprising a second inner surface surrounding a second outer surface of the second inner race, at least a portion of the second inner surface defining a second tapered region having decreasing diameter towards the second opening to the cavity, the decreasing diameter being with respect to the central axis. The assembly can also include a second plurality of clamping elements carried by the second inner race such that (i) movement of the second inner race proximally toward the second opening of the cavity engages the plurality of clamping elements against the second inner surface of the second outer race, the second inner surface urging the second plurality of clamping elements into the second central passage of the second inner race and towards the central axis, and (ii) movement of the second inner race distally away from the second opening of the cavity translates the second plurality of clamping elements along the second tapered region such that the increasing diameter allows the second plurality of clamping elements to move out of the second central passage and away from the central axis. In some embodiments, the assembly can also include a second biasing element that urges the second inner race proximally along the central axis toward the second opening. In some embodiments, the assembly can also include an end cap coupled to the second inner race and extending out of the second opening in the housing, the end cap defining a flange for applying a force to the second inner race in the distal direction to release an alignment guide.

In certain embodiments, the assembly can include an alignment guide, the alignment guide comprising a hollow shaft with a plurality of longitudinally-extending parallel grooves formed around an exterior portion of the hollow shaft, the hollow shaft being configured to be inserted into the central passage and the plurality of parallel grooves being configured to engage with the plurality of clamping elements. The plurality of parallel grooves can be spaced such that a misaligned engagement of the exterior portion with the plurality of clamping elements results in the biased movement of the inner race rotating the alignment guide about the central axis such that the plurality of clamping elements are engaged in the plurality of parallel grooves.

In some embodiments, the plurality of clamping elements can include ball bearings.

In another aspect, an assembly according to the present disclosure can include a housing having a cavity with an opening disposed at a distal end of the housing, as well as a first race disposed within the cavity and configured to translate relative to the housing along a longitudinal axis of the cavity extending from a proximal end thereof to the opening and remain locked against rotation relative to the housing about the longitudinal axis. The assembly can further include a plurality of bearing elements disposed within bores formed in the first race and configured to move radially relative to the longitudinal axis of the housing, as well as a second race disposed in the cavity of the housing and configured to remain fixed relative to the housing. Further, the first race can be biased distally toward the opening of the cavity. In addition, the second race can surround the first race and can include an inner surface having a tapered diameter that decreases from a proximal position to a distal position. Still further, the inner surface of the second race can be configured to contact the plurality of bearing elements as the first race moves distally relative to the second race such that inner surface of the second race urges the plurality of bearing elements radially inward.

In some embodiments, insertion of an alignment guide proximally into an opening in the first race can cause the first race to translate proximally until the plurality of bearing elements move radially outward a sufficient amount to allow the alignment guide to pass further.

In certain embodiments, the first race can be moveable in the proximal direction to an unclamped position where the plurality of bearing elements are allowed to move radially outward to permit insertion of an alignment guide proximally into an opening of the first race, and the first race can be moveable in the distal direction to a clamped position wherein the plurality of bearing elements are urged radially inward to apply a clamping force to the alignment guide.

In some embodiments, when an alignment guide is disposed such that the plurality of bearing elements prevent distal movement of the alignment guide, proximal translation of the first race can enable distal movement of the alignment guide. In some embodiments, the assembly can further include an end cap coupled to the first race, the end cap defining a flange for applying a force to the first race in the proximal direction to release an alignment guide.

In some embodiments, the housing can define a second opening into the cavity formed at the proximal end of the housing, the second opening being arranged such that an inner lumen of an alignment guide disposed in the housing is accessible through the second opening.

In certain embodiments, the assembly can further include a handle coupled to the housing, the handle can enable a user to apply torque to the housing, the torque being transferred to an alignment guide disposed in the housing via the plurality of bearing elements.

In some embodiments, the assembly can further include a second opening to the cavity formed at the proximal end of the housing, as well as a third race disposed in the cavity of the housing and configured to translate relative to the housing along the longitudinal axis of the cavity and remain locked against rotation relative to the housing about the longitudinal axis. The assembly can further include a second plurality of bearing elements disposed within bores formed in the third race and configured to move radially relative to the longitudinal axis of the housing, as well as a fourth race disposed in the cavity of the housing and configured to remain fixed relative to the housing. Further, the third race can be biased proximally toward the second opening of the cavity. In addition, the fourth race can surround the third race and can include an inner surface having a tapered diameter that decreases from a distal position to a proximal position. Still further, the inner surface of the fourth race can be configured to contact the second plurality of bearing elements as the third race moves proximally relative to the fourth race such that the inner surface of the fourth race urges the second plurality of bearing elements radially inward.

In some embodiments, the assembly can further include an end cap coupled to the third race and extending out of the second opening in the housing, the end cap defining a flange for applying a force to the third race in the distal direction to release an alignment guide.

In certain embodiments, the assembly can further include an alignment guide, the alignment guide comprising a hollow shaft with a plurality of longitudinally-extending parallel grooves formed around an exterior portion of the hollow shaft, the hollow shaft being configured to be inserted into the cavity of the housing and the plurality of parallel grooves being configured to engage with the plurality of bearing elements. In some embodiments, the plurality of parallel grooves can be spaced such that a misaligned engagement of the exterior portion with the plurality of bearing elements results in the biased movement of the first race rotating the alignment guide about the longitudinal axis such that the plurality of bearing elements are engaged in the plurality of parallel grooves.

In another aspect, a surgical method according to the present disclosure can include advancing a modular handle assembly distally over a proximal end of an alignment guide such that the alignment guide enters a cavity of the modular handle assembly and urges a race of the modular handle assembly in a proximal direction against a distal biasing force to permit a plurality of clamping elements coupled to the race to move radially outward from a central axis of the cavity and thereby permit proximal movement of the alignment guide relative to the race; and selectively locking the modular handle assembly relative to the alignment guide such that the modular handle assembly can be further advanced distally over the alignment guide but cannot be retracted proximally and cannot be rotated relative to the alignment guide.

In some embodiments, selectively locking the modular handle assembly can include urging the race in a distal direction to cause the plurality of clamping elements coupled to the race to move radially inward toward the central axis of the cavity and contact an outer surface of the alignment guide.

In certain embodiments, the method can further include unlocking the modular handle assembly relative to the alignment guide by moving the race of the modular handle assembly in a proximal direction to permit the plurality of clamping elements coupled to the race to move radially outward from the central axis of the cavity. In some embodiments, the method can further include rotating the modular handle assembly about the alignment guide while the modular handle assembly is unlocked relative to the alignment guide.

In some embodiments, moving the race of the modular handle assembly can include applying a proximal force to a flange of an end cap coupled to the race. In some embodiments, the method can further include selectively locking the modular handle assembly relative to the alignment guide to prevent relative rotation between the two components.

In another aspect, a surgical method according to the present disclosure can include unlocking a modular handle assembly, moving the modular handle assembly relative to an alignment guide such that the alignment guide passes through a cavity of the modular handle assembly, and locking the modular handle assembly relative to the alignment guide such that the modular handle assembly cannot be translated or rotated relative to the alignment guide.

In some embodiments, unlocking the modular handle assembly can include moving a first race in a proximal direction against a distal biasing force to permit a first plurality of clamping elements coupled to the first race to move radially outward from a central axis of a cavity of the modular handle assembly and moving a second race in a distal direction against a proximal biasing force to permit a second plurality of clamping elements coupled to the second race radially outward from the central axis of the cavity.

In certain embodiments, locking the modular handle assembly can include moving the first race in a distal direction to urge the first plurality of clamping elements radially inward toward a central axis of the cavity and moving the second race in a proximal direction to urge the second plurality of clamping elements radially inward toward the central axis of the cavity.

BRIEF DESCRIPTION OF DRAWINGS

This disclosure will be more fully understood from the following detailed description taken in conjunction with the accompanying drawings, in which:

FIG. 1B is a front view of the surgical tool assembly of FIG. 1A;

FIG. 1C is a side-view of the surgical tool assembly of FIG. 1A;

FIG. 1D is a rear-view of the surgical tool assembly of FIG. 1A;

FIG. 2A is an isometric view of the surgical tool assembly of FIG. 1A with the alignment guide removed from the handle with one-way bearing assembly;

FIG. 2B is cross-sectional view of the proximal end of the alignment guide taken along the line A-A of FIG. 2A;

FIG. 3B is a side-view of the exploded illustration of FIG. 3A;

FIG. 6A is a side cross-sectional view of the handle with fully-constrained bearing assembly taken along the line E-E in FIG. 5;

FIG. 6B is a side cross-sectional view of the handle with fully-constrained bearing assembly of FIG. 6A in an unclamped or compressed configuration; and FIG. 6C is a side cross-sectional view of the handle with fully-constrained bearing assembly of FIG. 6A in a clamped configuration about an elongated proximal end of an alignment guide.

DETAILED DESCRIPTION

Certain example embodiments will now be described to provide an overall understanding of the principles of the structure, function, manufacture, and use of the devices and methods disclosed herein. One or more examples of these embodiments are illustrated in the accompanying drawings. The devices and methods specifically described herein and illustrated in the accompanying drawings are non-limiting example embodiments and the scope of the present disclosure is defined solely by the claims. The features illustrated or described in connection with one example embodiment may be combined with the features of other embodiments. Such modifications and variations are intended to be included within the scope of the present disclosure.

Additionally, to the extent that linear, circular, or other dimensions are used in the description of the disclosed systems and methods, such dimensions are not intended to limit the types of shapes that can be used in conjunction with such systems and methods. Equivalents to such linear, circular, or other dimensions can be determined for any geometric shape. Further, in the present disclosure, like-numbered components of the embodiments generally have similar features. Still further, sizes and shapes of the systems, and the components thereof, can depend at least on the anatomy of the subject in which the systems will be used, the size and shape of components with which the devices will be used, and the methods and procedures in which the devices will be used.

Devices, systems, and methods for selectively coupling components, such as alignment guides or other tools to a modular handle for use in retaining and applying torque to the alignment guide or other tool are disclosed herein. In operation, the bearing assemblies disclosed herein can be used to receive a proximal end of an alignment guide or other instrument, with the bearing assembly securing the alignment guide or instrument upon insertion without any toggling of the alignment guide or instrument with respect to the bearing assembly (e.g., movement of the alignment guide or instrument in one direction into the bearing assembly can result in the alignment guide or instrument being secured without any possible subsequent movement of the alignment guide being possible). Similarly, once coupled, the alignment guide or instrument can be decoupled from the bearing assembly without any movement of the alignment guide or instrument with respect to the bearing assembly by depressing an endcap of the bearing assembly to release the internal clamping mechanism. This operation and related structural features, movements, and arrangements are discussed in more detail below.

Figure 1A:
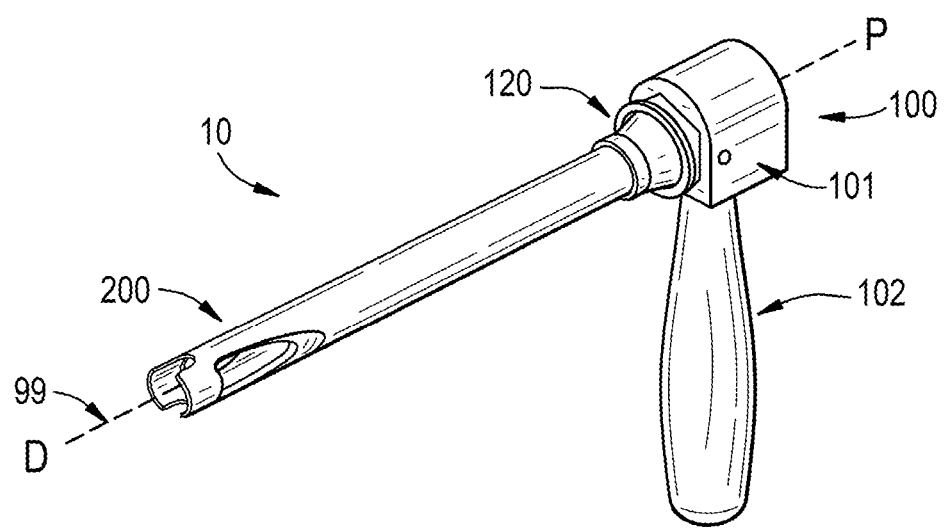
FIG. 1A is an isometric view of one embodiment of a surgical tool assembly including an alignment guide and handle with one-way bearing assembly according to aspects of the present disclosure.

FIG. 1A is an isometric view of one embodiment of a surgical tool assembly 10 including an alignment guide 200 and a one-way axial and radial bearing assembly 100 (hereinafter referred to interchangeably as "the bearing assembly 100") according to aspects of the present disclosure. The surgical tool assembly 10 can be any arrangement of the bearing assembly 100 and the alignment guide 200, for example, as a coupled arrangement (as shown in FIG. 1A) or uncoupled (as shown in FIG. 2A). The alignment guide 200 can be used to provide, for example, access to a polyaxial bone screw implanted in a patient during spine surgery. The alignment guide 200 can couple to the polyaxial bone screw inside the patient's body and can extend outside the patient's body, thereby providing a surgeon or other user with a means for manipulating the polyaxial bone screw position/orientation, providing access to the bone screw through an inner lumen of the alignment guide (e.g., for set screw application, etc.), etc. While the illustrated embodiment features the alignment guide 200, the bearing assemblies disclosed here can be utilized in combination with any of a variety of other types of surgical instruments that may benefit from selective coupling with other components, such as a modular handle for the application of torque, etc.

Returning to FIG. 1A, the bearing assembly 100 includes a housing 101, inside of which a proximal end of the alignment guide 200 is disposed and secured, as well as a handle 102 extending from the housing 101 and configured to enable a user of the bearing assembly 100 to position and/or deliver torque to the alignment guide 200. The bearing assembly 100 secures the alignment guide 200 inside such that the alignment guide cannot be removed from the bearing assembly without proximal depression of an end cap 120 that is configured to release the internal mechanism of the bearing assembly 100 that secures the alignment guide to the bearing assembly. The bearing assembly 100 also rotatably secures the alignment guide 200 about its central axis 99 such that torque applied to the bearing assembly via the handle 102 is delivered to the alignment guide. As a convention, the free end of the alignment guide is established as the distal end ('D' in FIG. 1A) and the opposite, captured end of the alignment guide 200 is established as the proximal end ('P' in FIG. 1A), and the same convention is used hereinafter for the bearing assembly 100 as well. FIGS. 1B, 1C, and 1D are, front, side, and rear views, respectively, of the surgical tool assembly 10 of FIG. 1A. FIGS. 1B and 1D illustrate that both the bearing assembly 100 and the alignment guide 200 can have a central passage 109 that extends entirely therethrough. In operation, this enables a user to insert an additional tool, such as a driver, through both the bearing assembly 100 and the alignment guide 200 in order to manipulate a fastener, shank, or other hardware inside of the proximal end of the alignment guide.

Insertion of the alignment guide 200 into the bearing assembly 100 involves translating a proximal end 210 of the alignment guide 200 into a central opening of the bearing assembly 100, as illustrated in FIG. 2A. In some embodiments, the endcap 120 is depressed proximally to facilitate the ability to insert the alignment guide 200 into the bearing assembly 100, but in some embodiments no actuation of the endcap 120 is required to insert the alignment guide 200 into the bearing assembly, with the endcap 120 only being used to release the alignment guide 200, as explained in more detail below. FIG. 2B is cross-sectional view of the proximal end 210 of the alignment guide 200 of FIG. 2A, which shows that the proximal end has an exterior surface with a plurality of longitudinal grooves 211 formed therein and forming a series of ridges 212 therebetween. In operation, and as explained in more detail below, the insertion of the alignment guide 200 into the bearing assembly 100 includes the longitudinal grooves 211 being engaged by locking elements (e.g., ball bearings) that are radially coupled with the bearing assembly such that the alignment guide cannot freely rotate inside the bearing assembly. Additionally, the insertion also causes the locking elements to clamp onto the alignment guide 200 (e.g., radially inward toward the central axis 99) in such a way that subsequent distal movement of the alignment guide relative to the bearing assembly 100 is prevented.

Figure 3A:
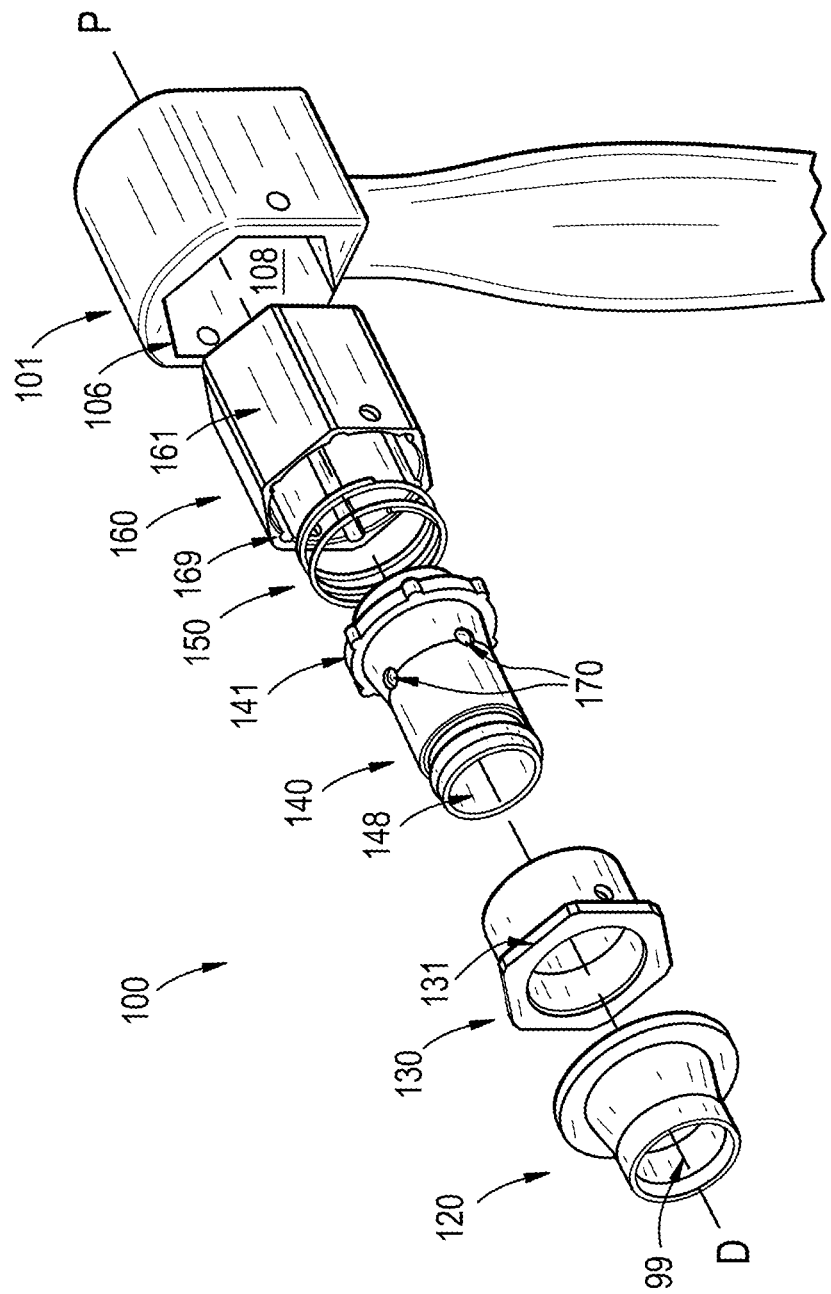
FIG. 3A is an isometric exploded view of the handle with one-way bearing assembly of FIG. 2A.

FIG. 3A shows an exploded view of the various internal components of the one-way axial bearing assembly 100 of FIG. 2A. The bearing assembly 100 includes the housing 101, an insert 160, a bias element 150, an inner race 140, an outer race 130, and the end cap 120. The housing 101 defines a cavity 108 with an open distal end through which the insert 160 is inserted along the central axis 99. The insert 160 includes flat sides 161 that are sized and shaped to abut corresponding flat sides 106 of the cavity 108 in the housing 101 such that, when inserted, the insert cannot rotate about the central axis 99 with respect to the housing. The inner race 140 is moveably disposed inside a cavity of the insert 160, with the inner race having a series of protrusions 141 extending radially from the exterior of the inner race. The protrusions 141 are configured to engage with corresponding longitudinal grooves 169 on an inner surface of the cavity of the insert 160 such that the inner race can translate along the central axis 99 with movement of the protrusions 141 along the corresponding longitudinal grooves 169, but rotational movement of the inner race relative to the insert about the central axis is prevented. Additionally, the bias element 150 is positioned in the cavity of the insert 160 proximal to inner race 140 such that the bias element urges the inner race distally and enables the inner race to be moved proximally against the force of the bias element 150. The inner race 140 also includes a central passageway 148 and a plurality of ball bearings 170 that are positioned or captured in bores of the inner race and able to partially extend into the central passageway 148.

The outer race 130 is configured to be inserted into the housing 101 and the insert 160 around the exterior of the inner race 140. The outer race 130 includes a distal flange that has flat edges 131 sized and shaped to be aligned with the flat sides 161 of the insert 160 when the outer race is disposed in the insert. The flat edges 131 also engage with the corresponding flat sides 106 of the cavity 108 in the housing 101 such that, when inserted, the outer race 130 cannot rotate in the housing 160. The flange having the flat edges 131 also locates the outer race 130 proximally against a distal face of the insert 160. Finally, the endcap 120 is configured to be threaded onto a distal end of the inner race 140 that protrudes distally beyond the distal face of the outer race 130. FIG. 3B is a side-view of the exploded illustration of FIG. 3A, showing how the components of bearing assembly 100 can be secured together using a series of holes 137, 167, 107 through which a locking member (e.g., pin, bolt, etc.) can be disposed. When the insert 160 is disposed in the housing 101, the hole 107 through the housing can be aligned with the hole 167 through the insert, and when the inner race 140 is disposed in the insert 160 and the outer race 130 is disposed around the inner race in the insert, the hole 137 in the outer race can also be aligned with the holes 167, 107 in the insert and housing. When aligned, a pin or other locking member can be placed through all three holes to prevent removal of any and all of the outer race 130, inner race 140, bias element 150, and insert 160 from the cavity of the housing 101.

Figure 3C:
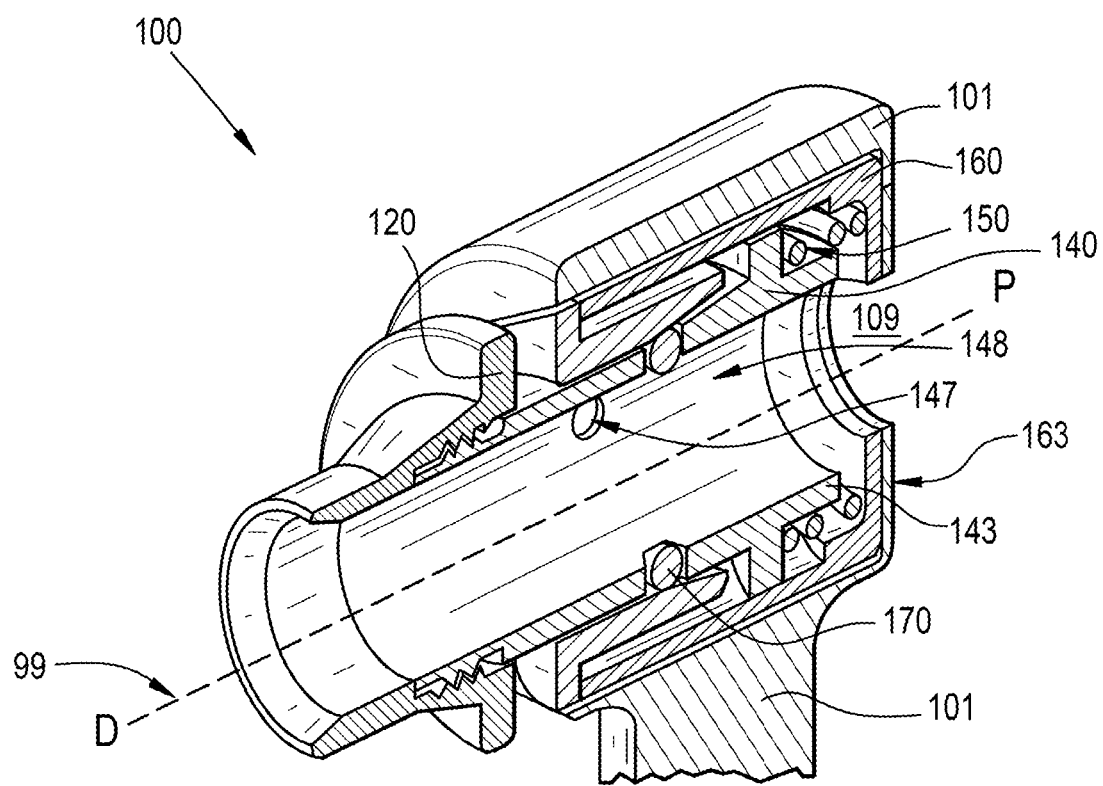
FIG. 3C is an isometric cross-sectional view of the handle with one-way bearing assembly taken along the line B-B of FIG. 2A.

FIG. 3C is an isometric cross-section illustration of the one-way axial bearing assembly 100 with all of the components assembled together. FIG. 3C shows that the proximal end 143 of the inner race 140 defines a stop position of the inner race in the insert 160 where proximal movement of the inner race against the bias element 150 is prevented due to contact of the proximal end 143 of the inner race with an inner distal-facing surface 163 of the proximal end of the insert 160. Also visible in FIG. 3C is the central passageway 148 of the inner race 140, which communicates with the bores 147 containing the ball bearings 170. FIG. 3C shows the ball bearings 170 in a clamped position where the ball bearings are held in a radially-inward position by the outer race 130, as explained in more detail below.

Figure 3D:
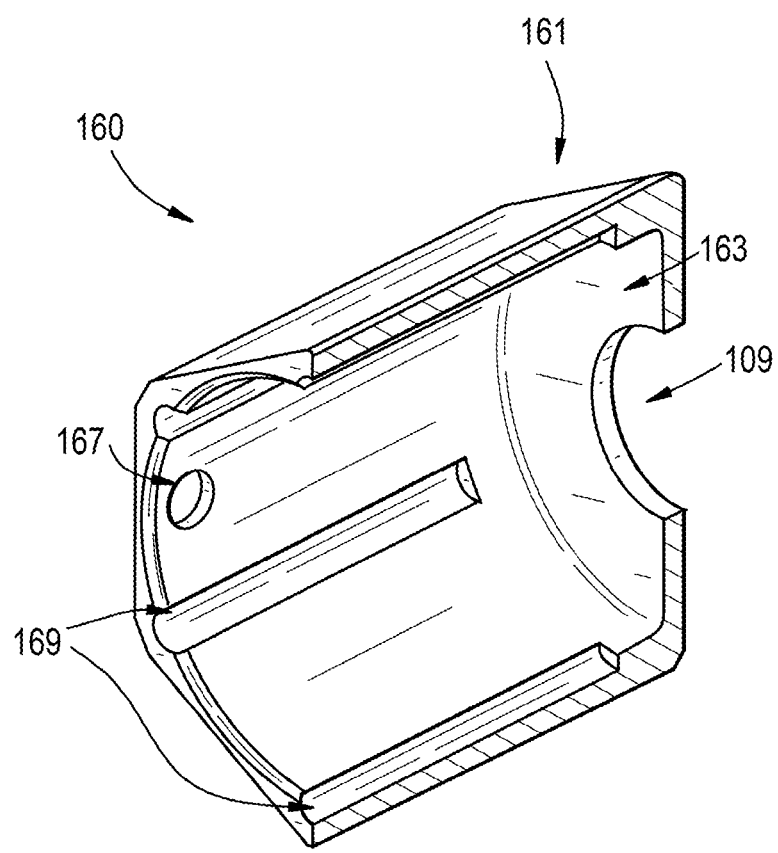
FIG. 3D is an isolated detail view of an insert component of the one-way bearing assembly of FIG. 3C.

FIG. 3D is an isometric cross-section of the insert 160, showing the flat sides 161, the longitudinal grooves 169, the distal-facing inner surface 163 formed in a proximal portion of the insert, and the hole 167. In some instances, the length of the longitudinal grooves 169 can be used alone (or in additional to the distal-facing inner surface 163) to define a stop position of the inner race 140 in the insert 160. The proximal portion of the insert 160 also defines an opening 109 that is present in both the distal end of the insert 160 and the distal end of the cavity 108 of the housing 101. The opening 109 is sized smaller than the distal end of the inner race 140 to allow access to the inner passage 219 of the alignment guide while still forming a stop to prevent distal movement of the inner race 140 in operation. The opening 109 is also sized smaller than the proximal end 210 of the alignment guide 200 to form a proximal stop for the alignment guide and define a fully-inserted position of the alignment guide 200 within the bearing assembly 100. In some embodiments, a proximal-facing surface of the housing 101 is configured to enable a user to impact the proximal-facing surface and direct an impulse to the alignment guide 200 via the terminal end of the alignment guide 200 being in direct contact with the proximal end of the insert 160, and the proximal end of the insert 160 being in direct contact with the proximal end of the housing 101.

Figure 3E:
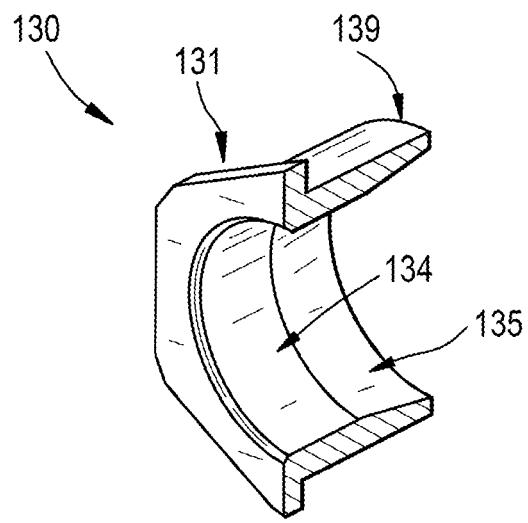
FIG. 3E is an isolated detail view of an outer race component of the one-way bearing assembly of FIG. 3C.
Figure 3F:
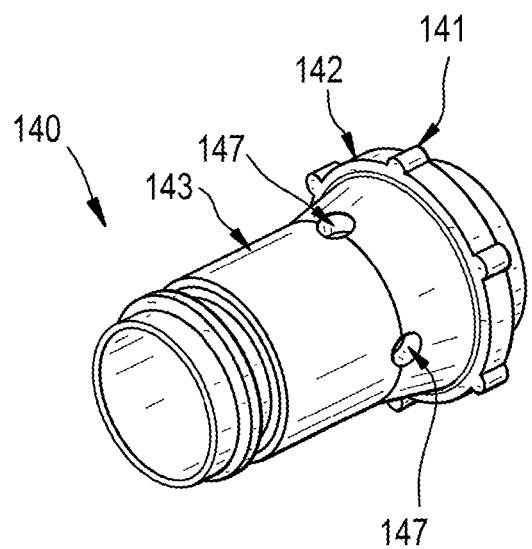
FIG. 3F is an isolated detail view of an inner race component of the one-way bearing assembly of FIG. 3C.

FIG. 3E is an isometric cross-section of the outer race 130, showing the flat edges 131. FIG. 3E also shows the inner surface of the outer race 130 that is configured to be positioned around the inner race 140. The inner surface includes a distal surface 134 portion and a proximal surface 135 portion. The proximal surface 135 is positioned to be disposed around the bores 147 of the inner race 140 and defines a tapered diameter that increases proximally from the diameter of the distal surface 134. In some instances, the distal surface 134 defines a constant diameter or is otherwise configured to enable the outer race 130 to move concentrically long the exterior of the inner race 140. FIG. 3F is an isometric view of the inner race 140 with the bores 147 and protrusions 141 visible. The inner race 140 has an exterior surface 143 that is sized and shaped to have the inner surface of the outer race 130 disposed around the exterior surface 143 with the inner race 140 being free to move along the central axis 99 relative to the outer race 130 when assembled. Additionally, the exterior surface 143 includes a flange 142 that extends radially outward and includes the protrusions 141. The outer race 130 can include a terminal proximal edge 139 that is configured to be a distal stop for the inner race 140 such that distal movement of the inner race with respect to the outer race 130 is prevented once the flange 142 contacts the terminal proximal edge 139, as shown in more detail in FIG. 4A.

Figure 4A:
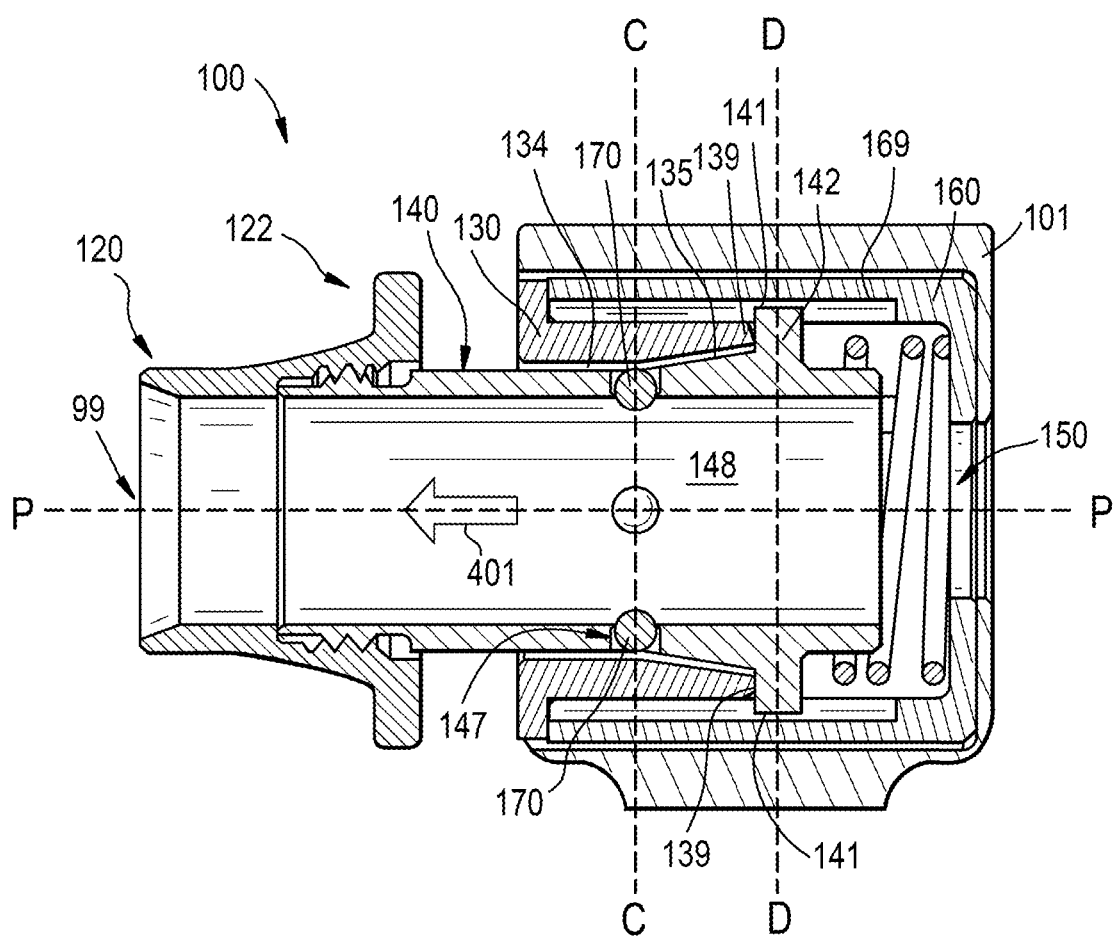
FIG. 4A is a side cross-sectional view of the handle with one-way bearing assembly of FIG. 3C in a fully extended or resting configuration.

FIG. 4A is a side cross-sectional view of the one-way axial bearing assembly 100 of FIG. 3C in a fully extended or resting configuration, such that the bias element 150 has moved the inner race 140 distally with respect to the housing 101, insert 160, and inner race 130 until the flange 142 of the inner race 140 abuts the terminal proximal edge 139 of the outer race 130. The distal movement (as indicated by arrow 401) of the inner race 140 slides the ball bearings 170 against the tapered distal surface 134 of the outer race 130 and the decreasing tapered diameter of the distal surface 134 forces the ball bearings radially inward in their bores 147, towards the central axis 99, and into the central passageway 148 of the inner race 140. In some instances, and as shown in FIG. 4A, the distal movement of the inner race 140 can translate the ball bearings 170 distally until the ball bearings are positioned against the distal surface 134 of the out race 130. In this position, without any taper on the distal surface 134, forcing of the ball bearings 170 radially outward against the distal surface 134 will not urge the inner race proximally. This position of the inner race 140 and ball bearings 170 can be described as a fully-extended or resting position, as this is the default position of the bearing assembly 100 without an alignment guide 200 inserted. Insertion of the alignment guide can begin with a user depressing the flange 122 of the end cap 120, as shown in FIG. 4B, or simply with the insertion of the proximal end 210 of the alignment guide 200 into the central passageway 148.

Figure 4B:
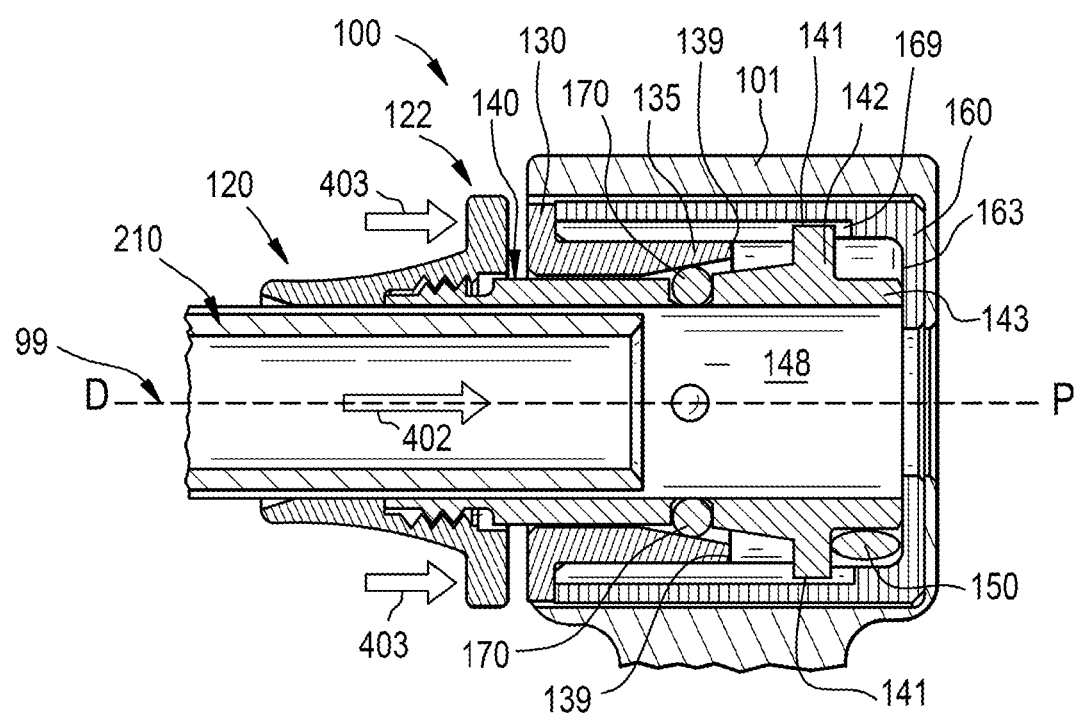
FIG. 4B is a side cross-sectional view of the handle with one-way bearing assembly of FIG. 4A in an unclamped or compressed configuration.

In FIG. 4B, a user depresses the endcap 120 proximally (arrows 403) and moves the inner race 140 proximally until the proximal end 143 of the inner race 140 contacts the inner distal-facing surface 163 of the proximal end of the insert 160. The proximal movement of the inner race 140 translates the ball bearings proximally along the proximal surface 135 of the outer race 130 and the increasing tapered diameter of the proximal surface 135 allows the ball bearings to move away from the central axis 99 and at least partially out of the central passage 148. This position can be described as a compressed or unclamped position. FIG. 4B also illustrates the proximal end 210 of the alignment guide being inserted proximally (as indicated by arrow 402) into the central passageway 148. Importantly, in some configurations, the user depressing the endcap 120 proximally is optional, and the proximal insertion 402 of the proximal end of the alignment guide 200 causes the proximal end 210 to contact the ball bearings 170 in the resting position (as shown in FIG. 4A), after which further proximal insertion of the alignment guide 200 drives the inner race 140 proximally until the ball bearings have moved sufficiently proximally along the inner surface 135 such that the ball bearings 170 are moved out of the central passageway 148 far enough for the proximal end 210 of the alignment guide 200 to be fully inserted into the central passageway, as shown in FIG. 4C.

Figure 4C:
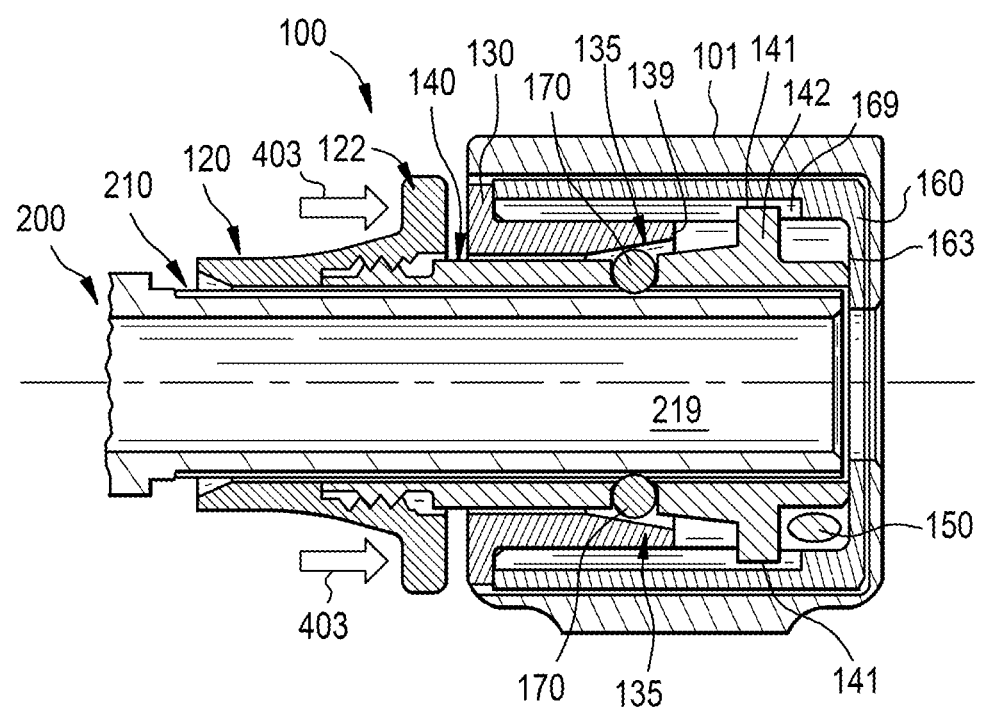
FIG. 4C is a side cross-sectional view of the handle with one-way bearing assembly of FIG. 4A in the unclamped or compressed configuration with a proximal end of the alignment guide of FIG. 2A fully inserted.

In FIG. 4C, the user can continue to depress the endcap 120 to keep the inner race 140 in the unclamped position as the alignment guide 200 is fully inserted, whereby the terminal proximal end of the alignment guide 200 abuts the inner distal-facing surface 163 of the proximal end of the insert 160. Regardless of whether the user depresses the endcap 120 to move the inner race 140 to the unclamped position or if insertion of the alignment guide 200 itself moves the inner race 140 proximally, the ball bearings 170 do not prevent movement of the alignment guide 200 in the proximal direction. However, once the user releases the endcap 120 or, in the case of alignment guide 200 insertion alone, once the alignment guide is fully inserted or proximal insertion is stopped, the bearing assembly 100 enters a clamped position with respect to the alignment guide 200, as shown in FIG. 4D, as a result of the force applied by bias element 150 on the inner race 140 in the distal direction.

Figure 4D:
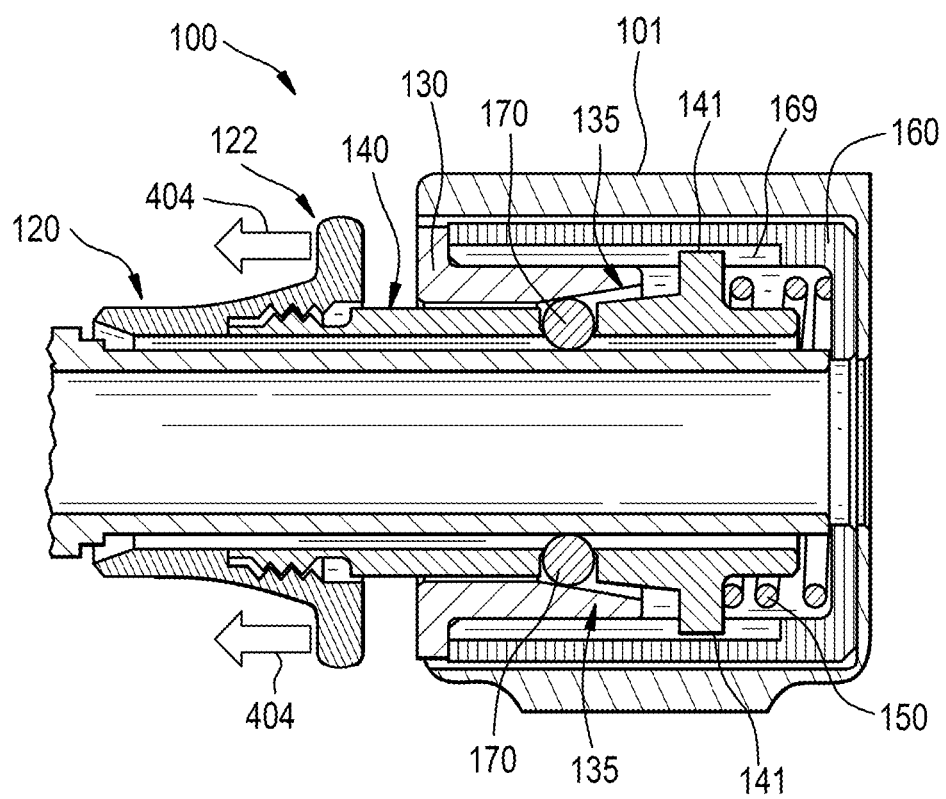
FIG. 4D is a side cross-sectional view of the handle with one-way bearing assembly of FIG. 4A in a clamped configuration with respect to the proximal end of the alignment guide.

In FIG. 4D, the alignment guide 200 is fully inserted and either the user has released the endcap 120 and the inner race 140 has moved distally (as indicated by arrows 404) to the position shown, or the illustrated position indicates the arrangement of the inner race 140 during insertion of the alignment guide 200, once the ball bearings 170 have moved sufficient to allow the alignment guide 200 to pass proximally. In FIG. 4D, the ball bearings 170 are positioned between the inner surface 135 and the proximal end 210 of the alignment guide 200 such that the ball bearings 170 are wedged by the tapered diameter of the proximal surface 135 of the outer race 130 and any further distal movement of the inner race 140 is prevented. Accordingly, the engagement also strongly clamps the ball bearings 170 against the surface of the proximal end 210 of the alignment guide 200 (e.g., perpendicular to the central axis 99), which prevents any distal movement of the alignment guide 200 with respect to the inner race 140 and, accordingly, with respect to the housing 101.

Figure 4E:
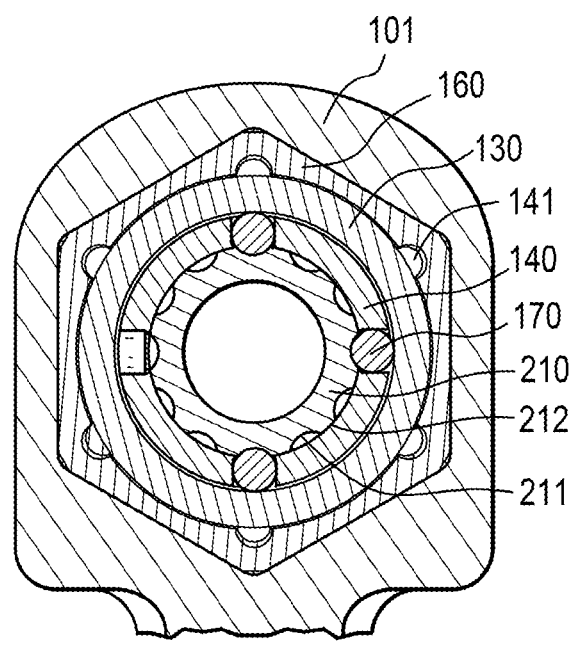
FIG. 4E is a front cross-sectional view of the handle with one-way bearing assembly taken along the line C-C of FIG. 4A showing the engagement of the ball bearings with longitudinal groove in the proximal end of the alignment guide.

FIG. 4E is a front cross-sectional view of the C-C plane drawn on the one-way axial bearing assembly 100 in FIG. 4D. In FIG. 4E the radial locking of the components of the bearing assembly and of the alignment guide 200 is visible. The ball bearings 170 are seated in the longitudinal grooves 211 of the proximal end 210 of the alignment guide 200 and prevent rotation of the alignment guide with respect to the inner race 140. The inner race 140 is rotatably coupled with the insert 160 via the protrusions being disposed in the grooves 169 of the insert 160, and the insert 160 is coupled with the housing 101 via the flat surfaces 161 in a manner that prevents relative rotation. Additionally, the interaction between the ball bearings 170 and the longitudinal grooves 211 and ridges 212 on the proximal end 210 of the alignment guide 200 can create a self-aligning interaction such that insertion of the alignment guide without the ball bearings 170 being seated in the longitudinal grooves 211 is self-corrected due to the instability of the ball bearings 170 contacting the ridges 212 and the ability of the alignment guide 200 to rotate relative to the inner race 140 when the ridges 212 contact the ball bearings 170. Accordingly, during insertion of the alignment guide 200 into the central passage 148 without user depression of the end cap 120, once the ball bearings 170 are moved by the ridges 212 of the alignment guide, even subtle rotation of the alignment guide in either direction moves the ball bearings 170 off the ridges 212 and into the longitudinal grooves 211. The ball bearings 170 entering the longitudinal grooves 211 allows the inner race 140 to move distally as the ball bearings can now move radially inward as urged by the bias element 150 (e.g., the longitudinal grooves 211 present a smaller diameter to the ball bearings 170 as compared to the ridges 212), and once the ball bearings 170 are in the longitudinal grooves 211 further rotation of the alignment guide 200 relative to the inner race 140 is not possible.

Figure 4F:
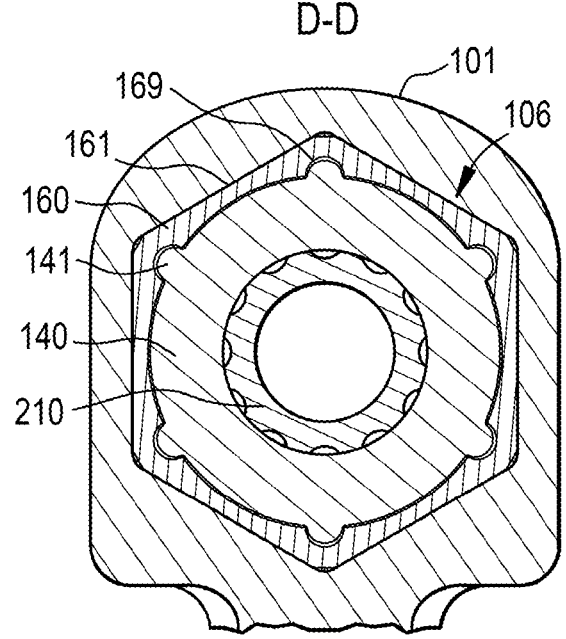
FIG. 4F is a front cross-sectional view of the handle with one-way bearing assembly taken along the line D-D of FIG. 4A showing the rotational-coupling between the inner race and the insert and between the insert and the housing.

There are a number of different techniques for coupling two components together in a manner that prevents relative rotation, many of which may be suitable for use with aspects of the present disclosure. Similarly, while the clamping elements discussed herein are shown as ball bearings, other clamping elements may be suitable with minor modification, such as rollers, etc. FIG. 4F is a front view cross-section of the D-D plane drawn on the one-way axial bearing assembly 100 in FIG. 4D more clearly showing the coupling between the inner race 140 and the insert 160, and the insert 160 with the housing 101, in a manner that prevents relative rotation therebetween.

Figure 4G:
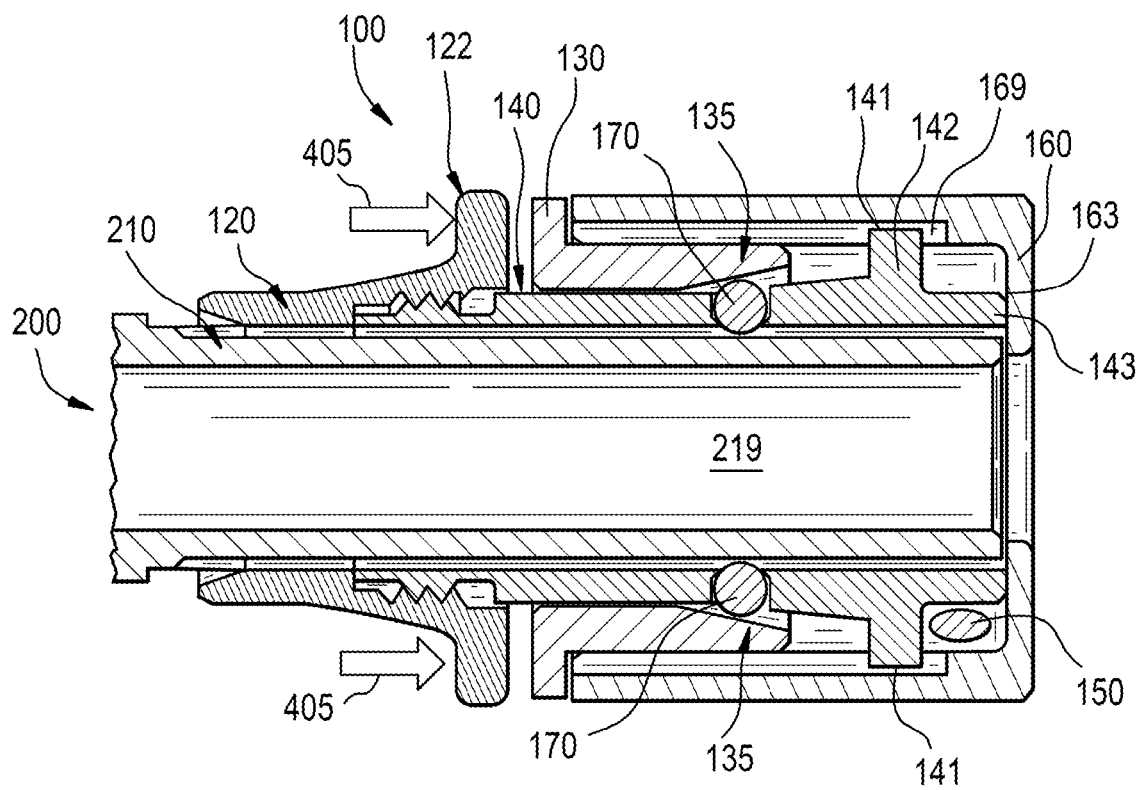
FIG. 4G is a side cross-sectional view of the handle with one-way bearing assembly of FIG. 4A in the unclamped or compressed configuration to allow removal of the alignment guide.
Figure 4H:
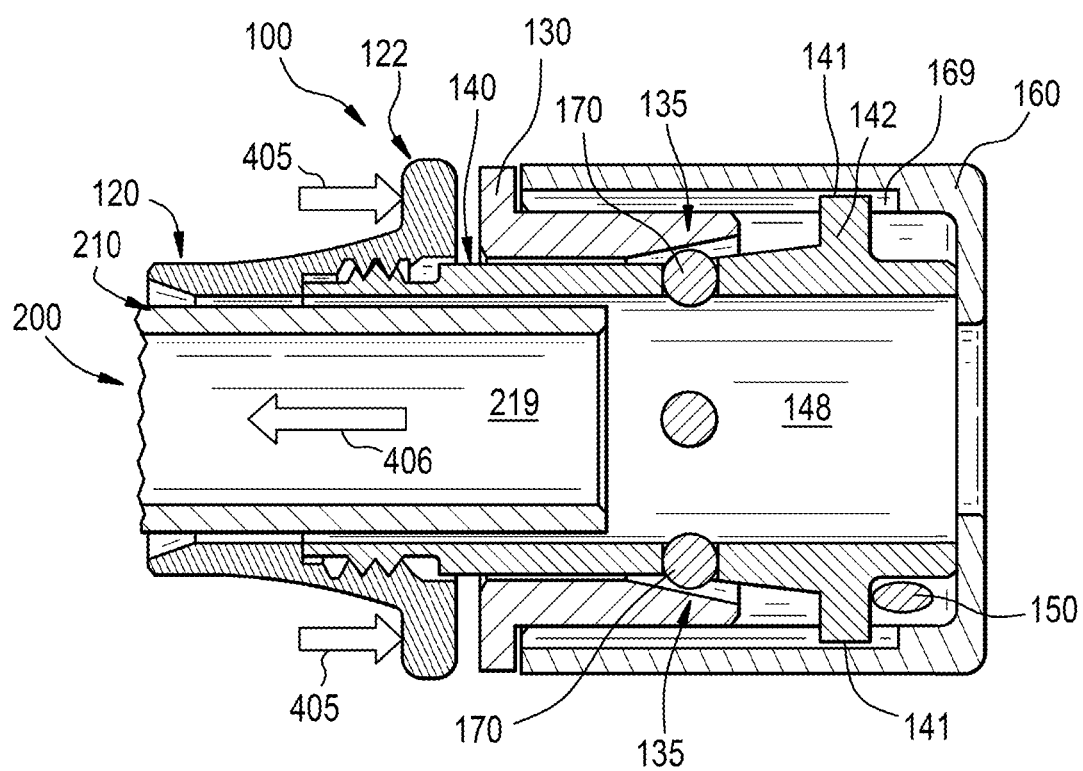
FIG. 4H is a side cross-sectional view of the handle with one-way bearing assembly of FIG. 4A in the unclamped or compressed configuration showing the removal of the alignment guide.

Turning to FIG. 4G, in order to free the alignment guide 200 from the bearing assembly, a user can depress the endcap 120 proximally (as indicated by arrows 405), which moves the inner race 140 to the unclamped position with the ball bearings 170 no longer being wedged against the alignment guide 200 due to the inner race 140 moving the ball bearings in the direction of the increasing tapered diameter of the inner surface 135, thereby allowing the ball bearings 170 to move radially outward and away from the alignment guide and removing the clamping force. With the endcap 120 depressed, the alignment guide 200 is free to be withdrawn from the central passage 148 of the inner race 140 and thereby removed from the bearing assembly 100, as shown in FIG. 4H (where the distal removal of the alignment guide 200 is indicated by arrow 406).

While the components of the bearing assembly 100 have been shown as individual elements, one or more of the components can be formed as common structures. For examples, in some embodiments, the housing 101 and the insert 160 can be a single structure or otherwise permanently joined. Additionally, while the bearing assembly 100 and the alignment guide are both illustrated as being circular, other shapes are possible, such as rectangular or ovoid, with such configurations having central passageways 148 sized and shaped to accept the shape of the alignment guide, and, in some examples, can also be similarly shaped inside the bearing assembly, such as the inner and outer races have rectangular shapes to match the shape of the alignment guide. In such examples, there may be no need for coupling the alignment guide in a manner that prevents rotation, as a rectangular or polygonal shaped alignment guide may already be rotationally constrained within a corresponding rectangular or polygonal shaped central passage. Also, while the bearing assembly 100 has been illustrated as a hand-held device with a handle 101, other uses are possible, such as integration into a stationary structure or surgical robot. The housing 101 can provide a cavity and a distal opening, and this arrangement can be provided in number of different structures.

Other embodiments of the present disclosure include a bearing assembly that incorporates dual bearing assemblies in an opposed design to fully constrain movement of an alignment guide relative to the bearing assembly (e.g., as opposed to the above-described configurations where movement in one direction can be permitted while movement in an opposite direction is prevented). Such a configuration can utilize two separate inner races aligned to form a single central passageway but oriented to move in opposite axial directions such that manual actuation of the inner races (e.g., pressing both towards each other) clears the central passage (e.g., no ball bearings are forced into the central passage from either inner race) to allow an alignment guide to be positioned in the central passage through both inner races. Thereafter, once the inner races are released, they are moved in opposite directions by respective bias elements to respective clamping positions that prevent subsequent axial movement of the alignment guide in either axial direction. Rotation can be prevented as well, as described herein. This bi-directional or dual-axial constraint of the alignment guide is in contrast to the single-directional or axial constraint created by the bearing assembly 100 of FIG. 4A, where once the ball bearings 170 are clamped down onto the alignment guide, further proximal movement of the alignment guide is still permitted until the alignment guide contacts the inner distal-facing surface 163 of the proximal end of the insert 160.

Figure 5:
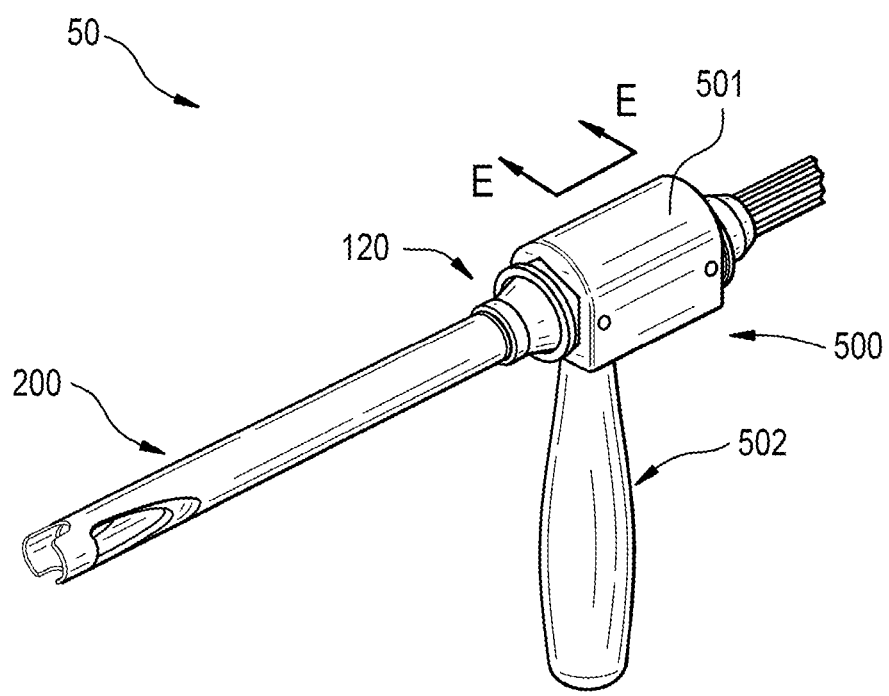
FIG. 5 is an isometric view of one embodiment of a surgical tool assembly including an alignment guide and handle with a fully-constrained bearing assembly according to aspects of the present disclosure.

One embodiment of surgical tool assembly including an alignment guide and handle with a fully-constrained axial bearing assembly 50 is shown in FIG. 5. The assembly 50 can include a fully-constrained or dual-axial bearing assembly 500, a housing 501, inside of which a proximal end of the alignment guide 200 is disposed and secured, as well as a handle 502 extending from the housing and configured to enable a user of the assembly 50 to position and/or deliver torque to the alignment guide 200.

A cross-section of the dual-axial bearing assembly 500 (e.g., a fully-constrained axial bearing, as rotation is prevented as well) is illustrated in FIGS. 6A-6C. Referring to FIG. 6A, the dual-axial bearing assembly 500 includes a distal bearing section 509a and a proximal bearing searing 509b, with the distal bearing section 509a being arranged similarly to the bearing assembly 100 of FIG. 4A, but with an addition proximal bearing searing 509b directly coupled to a common housing 501 and in an orientation that is flipped 180° about the proximal-distal direction of a common central axis 99. The common housing 501, as compared to the housing 101 of FIG. 4A, is extended in the proximal-distal direction to include an elongated cavity in which the components of the distal bearing section 509a are disposed and the components of the proximal bearing section 509b are disposed. As with the bearing assembly 100 of FIG. 4A, the housing 501 of the dual-axial bearing assembly 500 and one or both of the distal insert 506a and the proximal insert 560b can be integrated with the common housing 501. Additionally, and as shown in FIG. 6A, a common insert 560 is disposed within the common housing 501. In some instances this common insert 560 is separated into distal and proximal sections, but the cavity of the common housing 501 of FIG. 6A is a through bore and enables a common insert 560 to be disposed therein and coupled to the common housing 501 using, for example, the same locking body through holes discussed in view of FIG. 3A. Returning to FIG. 6A, the common insert 560 includes a central flange 563 that provides a distal face as a bearing surface, a distal bias element 550a, and a proximal face as a bearing surface for a proximal bias element 550b. The central flange 563 has a central opening to allow the respective central passageways 548a, 548b of the distal and proximal inner races 540a, 540b to be connected, however, the central flange 563 of the dual-axial bearing assembly 500 is shown to be slightly larger than the opening 109 of the bearing assembly 100 of FIG. 4A, as the central flange 563 of the dual-axial bearing assembly 500 is sized to allow an alignment guide 200 (shown in FIG. 5) to pass through the distal central passageway 548a and into the proximal central passageway 548b. Other embodiments include a common insert 560 without a central flange 563, with the distal bias element 550a and the proximal bias element 550b being either a single bias element or otherwise arranged to work together to bias the distal and proximal inner races 540a, 540b in their respective directions. In such a configuration, the inner stopping positions (e.g., the proximal-most location of the distal inner race 540a and the distal-most location of the proximal inner race 540b) can be defined by, for example, their respective interactions with the respective longitudinal grooves 569a, 569b in the common insert 560, or another structural interface.

Continuing to refer to the dual-axial bearing assembly 500 of FIG. 6A, the distal bearing section 509a includes a distal inner race 540a positioned in a proximal section of the common insert 560, and includes a flange 541a and protrusions 542a that are disposed in and travel along distal longitudinal grooves 569a in the common insert 560. The distal bearing section 509a also includes a distal outer race 530a around the distal inner race 540a, with the distal inner race 540a and the distal outer race 530a being arranged to function similar to the outer and inner races 130, 140 of the bearing assembly 100, such that ball bearings 570a in the inner races are moved into the distal inner passage 548a with distal movement of the distal inner race 540a with respect to the distal outer race 530a due to the ball bearings 570a engaging with a tapered proximal inner surface 535a of the distal outer race 530a. A distal endcap 520a is coupled with the distal end of the distal inner race 540a to enable a user to depress the distal inner race 540a in the proximal direction against the distal bias element until the distal inner race 540a contacts the central flange 563 in a fully compressed or unclamped position. The proximal bearing section 509b is arranged similarly, with a proximal inner race 540b disposed inside of a stationary or fixed proximal outer race 530b, with the proximal inner race 540b having ball bearings 570b that are engaged with a distal inner surface 535b of the proximal outer race 530b such that the proximal movement of the proximal inner race 540b under the urging of the proximal bias element 550b moves the ball bearings 570b into the proximal central passage 548 and a user's depressing of the proximal endcap 520b attached the proximal inner race 540b moves the proximal inner race 540b distally where the tapering of the distal inner surface 535b allows the ball bearings 570b to move radially away from the central axis 99.

In operation, and as shown in FIG. 6B, a user squeezes the distal endcap 520a and the proximal endcap 520b towards each other (as indicated by opposed arrows 505a and 505b), which compresses both the distal bias element 550a and the proximal bias element 550b until the distal inner race 540a is moved to a proximal-most position in the common insert 560 (e.g. the proximal end of the distal inner race 540a contacts the distal-facing surface of the central flange 563) and the proximal inner race 540b is moved to a distal-most position in the common insert 560 (e.g. the distal end of the proximal inner race 540b contacts the proximal-facing surface of the central flange 563). In this configuration that is shown in FIG. 6B, the ball bearings 570a of the distal inner race 540a are free to move out of the distal inner passage 548a and the ball bearings 570b of the proximal inner race 540b are free to move out of the proximal inner passage 548a. Accordingly, in this arrangement, an alignment guide 200 (shown in FIG. 5) is free to be inserted into the dual-axial bearing assembly 500 from either direction and to any axial position, and once the alignment guide is inserted past both the ball bearings 570a of the distal inner race 540a and the ball bearings 570b of the proximal inner race 540b, the user can release the squeezing force on both the distal endcap 520a and the proximal endcap 520b. This allows both (i) the distal bias element 550a to move the distal inner race 540a in the distal direction, thereby clamping the ball bearings 570a onto the alignment guide and preventing distal movement of the alignment guide, and (ii) the proximal bias element 550b to move the proximal inner race 540b in the proximal direction, thereby clamping the ball bearings 570b onto the alignment guide and preventing proximal movement of the alignment guide. This fully-clamped position of the dual-axial bearing assembly 500 is illustrated in FIG. 6C.

In FIG. 6C, an elongated end 210' of an alignment guide 200' is captured by the dual-axial bearing assembly 500 such that an inner passage 219' of the alignment guide 200' is disposed through the entire central passage 548a of the distal inner race 540a and almost all of the central passage 548b of the proximal inner race 540b. The distal bias element 550a pushes the distal inner race 540a in the distal direction (as indicated by arrows 506a) and the proximal bias element 550b pushes the proximal inner race 540b in the proximal direction (as indicated by arrows 506b). In this configuration, neither proximal nor distal movement of the alignment guide 200' is possible. Additionally, longitudinal grooves in the elongated proximal end 210' of the alignment guide 200' are engaged with both the ball bearings 570a of the distal inner race 540a and the ball bearings 570b of the proximal inner race 540b such that rotation of the alignment guide 200' with respect to the dual-axial bearing assembly 500 is prevented.

While the bearing assembly 100 of FIG. 4A and the dual-axial bearing assembly 500 of FIG. 6A are illustrated as being user-actuated, either or both of these devices can be actuated by an automated mechanism such as a surgical robot or any mechanical actuator coupled to (or in place of) the end cap. For example, an electric motor, such as a Lorentz force actuator, can be integrated with either bearing assembly such that movement of the endcap to release the alignment guide can be triggered with an electrical signal that generates a force on a coil integrated with the inner race to move the inner race against the bias element. Such an actuator can also be used in the opposite direction to ensure complete locking of the inner race by assisting the bias element and delivering additional force onto the inner race after the inner race is moved to the clamping position. Additionally, while the bearing assembly 100 of FIG. 4A and the dual-axial bearing assembly 500 of FIG. 6A are illustrated as having 4 ball bearings in their respective inner races, any number of locking elements is conceived, including 1, 2, 3, or 5 or more ball bearings or other locking elements. Additionally, while each inner race is shown as having a single annular bank of ball bearings, it is conceived that two or more banks can be used with, for example, larger diameter ball bearings that enable the tapered surface of the outer race to engage with two sizes of ball bearings simultaneously.

Additionally, it is within the scope of this disclosure to include a lock or other preventative mechanism for preventing unwanted depression of an endcap or a mechanism for holding an endcap in an unclamped position until released. While the bias elements are illustrated as being springs this is only a representative example of a bias element, and any number of different bias elements may be suitable for use with the bearing assembly 100 of FIG. 4A and the dual-axial bearing assembly 500 of FIG. 6A, such as pneumatic springs or magnets. Additionally, while the bearing assembly 100 of FIG. 4A and the dual-axial bearing assembly 500 of FIG. 6A are each illustrated as having a single inner race for each axial direction that is constrained, it is also possible to have two or more sequential inner races that each operate independently in order to more securely clamp onto an elongated alignment guide.

As noted above, any of a variety of surgical procedures can be performed utilizing the surgical tools described herein. In particular, the bearing assemblies disclosed herein can be utilized in connection with a variety of surgical instruments that can benefit from selective coupling with another instrument, such as a modular handle for application of torque/counter-torque, etc. These can include the alignment guides featured in the illustrated embodiments above, but also other instruments, such as drivers, other guide tubes, etc. The embodiments disclosed herein can find utility in various spine surgeries, such as in connection with open and/or minimally-invasive surgeries for treatment of acute and chronic instabilities or deformities of the spine. Alternative orthopedic applications and other types of surgeries can also benefit from use of the embodiments disclosed herein.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments, devices, and systems disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices, systems, and methods disclosed herein can be used in minimally-invasive surgery and/or open surgery. While the devices and methods disclosed herein are generally described in the context of orthopedic surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

The embodiments of the present disclosure described above are intended to be merely examples; numerous variations and modifications are possible and considered within the scope of this disclosure. Accordingly, the disclosure is not to be limited by what has been particularly shown and described. All publications and references cited herein are expressly incorporated by reference in their entirety, except for any definitions, subject matter disclaimers or disavowals, and except to the extent that the incorporated material is inconsistent with the express disclosure herein, in which case the language in this disclosure controls.

Examples of the above-described embodiments can include the following:

1. An assembly, comprising:
    a housing defining a cavity with a central axis extending from a proximal end of the housing to a distal end of the housing, as well as an opening to the cavity formed at the distal end of the housing;
    an inner race disposed in the cavity of the housing and defining an interface between the housing and the inner race, the interface enabling translation of the inner race along the central axis and resisting rotation of the inner race about the central axis, the inner race comprising an inner surface defining a central passage configured to receive a portion of an alignment guide;
    a biasing element that urges the inner race distally along the central axis toward the opening;
    an outer race disposed in the cavity and fixed relative to the housing, the outer race including an inner surface surrounding an outer surface of the inner race, at least a portion of the inner surface defining a tapered region having decreasing diameter towards the opening to the cavity;
    a plurality of clamping elements carried by the inner race such that (i) movement of the inner race distally toward the opening of the cavity engages the plurality of clamping elements against the inner surface of the outer race, the inner surface of the outer race urging the plurality of clamping elements into the central passage of the inner race and towards the central axis, and (ii) movement of the inner race proximally away from the opening of the cavity translates the plurality of clamping elements along the tapered region such that the increasing diameter allows the plurality of clamping elements to move out of the central passage and away from the central axis;

wherein, after insertion of an alignment guide sized to contact the plurality of clamping elements into the central passage of the inner race in the proximal direction, engagement of the plurality of clamping elements with the tapered region prevents movement of the inner race and the alignment guide in the distal direction.

2. The assembly of claim 1, wherein insertion of an alignment guide sized to contact the plurality of clamping elements into the central passage of the inner race in the proximal direction causes the inner race to be translated proximally with the alignment guide until the clamping elements are allowed to move sufficiently out of the central passage to allow the alignment guide to pass further into the central passage and the cavity.

3. The assembly of any of claims 1 to 2,
   wherein the inner race is moveable in the proximal direction to an unclamped position where the plurality of clamping elements are allowed to move away from the central axis to permit insertion of an alignment guide sized to contact the plurality of clamping elements into the central passage of the inner race in the proximal direction, and
   wherein the inner race is moveable in the distal direction to a clamped position wherein the plurality of clamping elements are urged towards the central axis to apply a clamping force to the alignment guide.

4. The assembly of any of claims 1 to 3,
   wherein the central passage of the inner race is cylindrical,
   wherein the plurality of clamping elements are circumferentially fixed with respect to the inner race; and
   wherein insertion of a cylindrical alignment guide comprising one or more grooves sized to receive and contact the plurality of clamping elements causes the cylindrical alignment guide to be rotationally fixed about the central axis with respect to the housing.

5. The assembly of any of claims 1 to 4, wherein, when an alignment guide is disposed in the central passage such that the plurality of clamping elements prevent movement of the alignment guide in the distal direction, translation of the inner race in the proximal direction enables removal of the alignment guide in the distal direction.

6. The assembly of claim 5, further comprising an end cap coupled to the inner race and extending out of the opening in the housing, the end cap defining a flange for applying a force to the inner race in the proximal direction to release an alignment guide.

7. The assembly of any of claims 1 to 6, wherein the biasing element is a compression spring.

8. The assembly of any of claims 1 to 7, wherein the housing comprises an insert disposed in an outer cavity of the housing, the insert defining the cavity containing the inner race to be inserted through the opening of the housing, the insert defining an inner cavity.

9. The assembly of claim 8,
   wherein the outer cavity defines a non-circular cross section parallel to the central axis, and
   wherein an exterior of the insert is configured to interface with the outer cavity such that the insert is rotationally fixed in the outer cavity about the central axis.

10. The assembly of any of claims 1 to 9,
    wherein the cavity comprises a plurality of grooves extending parallel to the central axis, and
    wherein the interface of the inner race comprises a plurality of protrusions, each of the plurality of protrusions being translatably disposed in a corresponding one of the plurality of protrusions.

11. The assembly of any of claims 1 to 10,
    wherein the housing defines a stop surface in the cavity positioned to be contacted by an end of an alignment guide such that the stop surface defines a position of maximum insertion of the alignment guide in the cavity, and
    wherein the stop enables an impact force to be directed from the housing to an end of a fully inserted alignment guide via the stop.

12. The assembly of any of claims 1 to 11, wherein the housing defines a second opening into the cavity formed at the proximal end of the housing, the second opening being arranged such that an inner lumen of an alignment guide disposed in the central cavity of the inner race is accessible through the second opening.

13. The assembly of any of claims 1 to 12, wherein the outer race is rotationally fixed in the cavity about the central axis.

14. The assembly of any of claims 1 to 13, wherein the outer race is configured to abut the inner race when the inner race is biased distally to a fully extended position.

15. The assembly of claim 14, wherein, in the fully extended position, the plurality of clamping members are urged toward a maximally inward position with respect to the central axis.

16. The assembly of claim 14,
    wherein the inner race is configured to abut the housing when the inner race is moved proximally to a fully compressed position, and
    wherein, in the fully compressed position, the plurality of clamping elements are free to move to a maximally outward position with respect to the central axis.

17. The assembly of any of claims 1 to 16, comprising a handle coupled to the housing, the handle configured to enable a user to apply torque to the housing, the torque being transferred to an alignment guide disposed in the central passage via the interface of the inner race and the plurality of clamping elements.

18. The assembly of any of claims 1 to 17, further comprising:
    a second opening to the cavity formed at the proximal end of the housing;
    a second inner race disposed in the cavity of the housing and translatable in the cavity along the central axis, the second inner race comprising a second inner surface defining a second central passage concentrically aligned with the central passage and configured to receive the portion of an alignment guide after passing through the central passage of the inner race;
    a second outer race disposed in the cavity and fixed along the central axis, the second outer race comprising a second inner surface surrounding a second outer surface of the second inner race, at least a portion of the second inner surface defining a second tapered region having decreasing diameter towards the second opening to the cavity, the decreasing diameter being with respect to the central axis;
    a second plurality of clamping elements carried by the second inner race such that (i) movement of the second inner race proximally toward the second opening of the cavity engages the plurality of clamping elements against the second inner surface of the second outer race, the second inner surface urging the second plurality of clamping elements into the second central passage of the second inner race and towards the central axis, and (ii) movement of the second inner race distally away from the second opening of the cavity translates the second plurality of clamping elements along the second tapered region such that the increasing diameter allows the second plurality of clamping elements to move out of the second central passage and away from the central axis.

19. The assembly of claim 18, further comprising a second biasing element that urges the second inner race proximally along the central axis toward the second opening.

20. The assembly of claim 18, further comprising an end cap coupled to the second inner race and extending out of the second opening in the housing, the end cap defining a flange for applying a force to the second inner race in the distal direction to release an alignment guide.

21. The assembly of any of claims 1 to 20, further comprising an alignment guide, the alignment guide comprising a hollow shaft with a plurality of longitudinally-extending parallel grooves formed around an exterior portion of the hollow shaft, the hollow shaft being configured to be inserted into the central passage and the plurality of parallel grooves being configured to engage with the plurality of clamping elements.

22. The assembly of claim 21, wherein the plurality of parallel grooves are spaced such that a misaligned engagement of the exterior portion with the plurality of clamping elements results in the biased movement of the inner race rotating the alignment guide about the central axis such that the plurality of clamping elements are engaged in the plurality of parallel grooves.

23. The assembly of any of claims 1 to 22, wherein the plurality of clamping elements comprises ball bearings.

24. An assembly, comprising:
    a housing having a cavity with an opening disposed at a distal end of the housing;
    a first race disposed within the cavity and configured to translate relative to the housing along a longitudinal axis of the cavity extending from a proximal end thereof to the opening and remain locked against rotation relative to the housing about the longitudinal axis;
    a plurality of bearing elements disposed within bores formed in the first race and configured to move radially relative to the longitudinal axis of the housing;
    a second race disposed in the cavity of the housing and configured to remain fixed relative to the housing;
    wherein the first race is biased distally toward the opening of the cavity;
    wherein the second race surrounds the first race and includes an inner surface having a tapered diameter that decreases from a proximal position to a distal position;
    wherein the inner surface of the second race is configured to contact the plurality of bearing elements as the first race moves distally relative to the second race such that inner surface of the second race urges the plurality of bearing elements radially inward.

25. The assembly of claim 24, wherein insertion of an alignment guide proximally into an opening in the first race causes the first race to translate proximally until the plurality of bearing elements move radially outward a sufficient amount to allow the alignment guide to pass further.

26. The assembly of any of claims 24 to 25,
    wherein the first race is moveable in the proximal direction to an unclamped position where the plurality of bearing elements are allowed to move radially outward to permit insertion of an alignment guide proximally into an opening of the first race, and
    wherein the first race is moveable in the distal direction to a clamped position wherein the plurality of bearing elements are urged radially inward to apply a clamping force to the alignment guide.

27. The assembly of any of claims 24 to 26, wherein, when an alignment guide is disposed such that the plurality of bearing elements prevent distal movement of the alignment guide, proximal translation of the first race enables distal movement of the alignment guide.

28. The assembly of claim 27, further comprising an end cap coupled to the first race, the end cap defining a flange for applying a force to the first race in the proximal direction to release an alignment guide.

29. The assembly of any of claims 24 to 28, wherein the housing defines a second opening into the cavity formed at the proximal end of the housing, the second opening being arranged such that an inner lumen of an alignment guide disposed in the housing is accessible through the second opening.

30. The assembly of any of claims 24 to 29, further comprising a handle coupled to the housing, the handle configured to enable a user to apply torque to the housing, the torque being transferred to an alignment guide disposed in the housing via the plurality of bearing elements.

31. The assembly of any of claims 24 to 30, further comprising:
    a second opening to the cavity formed at the proximal end of the housing;
    a third race disposed in the cavity of the housing and configured to translate relative to the housing along the longitudinal axis of the cavity and remain locked against rotation relative to the housing about the longitudinal axis;
    a second plurality of bearing elements disposed within bores formed in the third race and configured to move radially relative to the longitudinal axis of the housing;
    a fourth race disposed in the cavity of the housing and configured to remain fixed relative to the housing;
    wherein the third race is biased proximally toward the second opening of the cavity;
    wherein the fourth race surrounds the third race and includes an inner surface having a tapered diameter that decreases from a distal position to a proximal position;
    wherein the inner surface of the fourth race is configured to contact the second plurality of bearing elements as the third race moves proximally relative to the fourth race such that the inner surface of the fourth race urges the second plurality of bearing elements radially inward.

32. The assembly of claim 31, further comprising an end cap coupled to the third race and extending out of the second opening in the housing, the end cap defining a flange for applying a force to the third race in the distal direction to release an alignment guide.

33. The assembly of any of claims 24 to 32, further comprising an alignment guide, the alignment guide comprising a hollow shaft with a plurality of longitudinally-extending parallel grooves formed around an exterior portion of the hollow shaft, the hollow shaft being configured to be inserted into the cavity of the housing and the plurality of parallel grooves being configured to engage with the plurality of bearing elements.

34. The bearing assembly of claim 33, wherein the plurality of parallel grooves are spaced such that a misaligned engagement of the exterior portion with the plurality of bearing elements results in the biased movement of the first race rotating the alignment guide about the longitudinal axis such that the plurality of bearing elements are engaged in the plurality of parallel grooves.

35. A surgical method, comprising:
    advancing a modular handle assembly distally over a proximal end of an alignment guide such that the alignment guide enters a cavity of the modular handle assembly and urges a race of the modular handle assembly in a proximal direction against a distal biasing force to permit a plurality of clamping elements coupled to the race to move radially outward from a central axis of the cavity and thereby permit proximal movement of the alignment guide relative to the race; and
    selectively locking the modular handle assembly relative to the alignment guide such that the modular handle assembly can be further advanced distally over the alignment guide but cannot be retracted proximally and cannot be rotated relative to the alignment guide.

36. The method of claim 35, wherein selectively locking the modular handle assembly includes urging the race in a distal direction to cause the plurality of clamping elements coupled to the race to move radially inward toward the central axis of the cavity and contact an outer surface of the alignment guide.

37. The method of any of claims 35 to 36, further comprising unlocking the modular handle assembly relative to the alignment guide by moving the race of the modular handle assembly in a proximal direction to permit the plurality of clamping elements coupled to the race to move radially outward from the central axis of the cavity.

38. The method of claim 37, further comprising rotating the modular handle assembly about the alignment guide while the modular handle assembly is unlocked relative to the alignment guide.

39. The method of any of claims 35 to 38, wherein moving the race of the modular handle assembly includes applying a proximal force to a flange of an end cap coupled to the race.

40. The method of claim 38, further comprising selectively locking the modular handle assembly relative to the alignment guide to prevent relative rotation between the two components.

41. A surgical method, comprising:
    unlocking a modular handle assembly;
    moving the modular handle assembly relative to an alignment guide such that the alignment guide passes through a cavity of the modular handle assembly; and
    locking the modular handle assembly relative to the alignment guide such that the modular handle assembly cannot be translated or rotated relative to the alignment guide.

42. The method of claim 41, wherein unlocking the modular handle assembly includes moving a first race in a proximal direction against a distal biasing force to permit a first plurality of clamping elements coupled to the first race to move radially outward from a central axis of a cavity of the modular handle assembly and moving a second race in a distal direction against a proximal biasing force to permit a second plurality of clamping elements coupled to the second race radially outward from the central axis of the cavity.

43. The method of any of claims 41 to 42, wherein locking the modular handle assembly includes moving the first race in a distal direction to urge the first plurality of clamping elements radially inward toward a central axis of the cavity and moving the second race in a proximal direction to urge the second plurality of clamping elements radially inward toward the central axis of the cavity.

What is claimed is:
1. An assembly, comprising:
   a housing defining a cavity with a central axis extending from a proximal end of the housing to a distal end of the housing, as well as an opening to the cavity formed at the distal end of the housing;
   an inner race disposed in the cavity of the housing and defining an interface between the housing and the inner race, the interface enabling translation of the inner race along the central axis and resisting rotation of the inner race about the central axis, the inner race comprising an inner surface defining a central passage configured to receive a portion of an alignment guide;
   a biasing element that urges the inner race distally along the central axis toward the opening;
   an outer race disposed in the cavity and fixed relative to the housing, the outer race including an inner surface surrounding an outer surface of the inner race, at least a portion of the inner surface defining a tapered region having decreasing diameter towards the opening to the cavity;
   a plurality of clamping elements carried by the inner race such that (i) movement of the inner race distally toward the opening of the cavity engages the plurality of clamping elements against the inner surface of the outer race, the inner surface of the outer race urging the plurality of clamping elements into the central passage of the inner race and towards the central axis, and (ii) movement of the inner race proximally away from the opening of the cavity translates the plurality of clamping elements along the tapered region such that the increasing diameter allows the plurality of clamping elements to move out of the central passage and away from the central axis;
   wherein, after insertion of an alignment guide sized to contact the plurality of clamping elements into the central passage of the inner race in the proximal direction, engagement of the plurality of clamping elements with the tapered region prevents movement of the inner race and the alignment guide in the distal direction.

2. The assembly of claim 1, wherein insertion of an alignment guide sized to contact the plurality of clamping elements into the central passage of the inner race in the proximal direction causes the inner race to be translated proximally with the alignment guide until the clamping elements are allowed to move sufficiently out of the central passage to allow the alignment guide to pass further into the central passage and the cavity.

3. The assembly of claim 1,
wherein the inner race is moveable in the proximal direction to an unclamped position where the plurality of clamping elements are allowed to move away from the central axis to permit insertion of an alignment guide sized to contact the plurality of clamping elements into the central passage of the inner race in the proximal direction, and
wherein the inner race is moveable in the distal direction to a clamped position wherein the plurality of clamping elements are urged towards the central axis to apply a clamping force to the alignment guide.

4. The assembly of claim 1,
wherein the central passage of the inner race is cylindrical,
wherein the plurality of clamping elements are circumferentially fixed with respect to the inner race; and
wherein insertion of a cylindrical alignment guide comprising one or more grooves sized to receive and contact the plurality of clamping elements causes the cylindrical alignment guide to be rotationally fixed about the central axis with respect to the housing.

5. The assembly of claim 1, wherein, when an alignment guide is disposed in the central passage such that the plurality of clamping elements prevent movement of the alignment guide in the distal direction, translation of the inner race in the proximal direction enables removal of the alignment guide in the distal direction.

6. The assembly of claim 5, further comprising an end cap coupled to the inner race and extending out of the opening in the housing, the end cap defining a flange for applying a force to the inner race in the proximal direction to release an alignment guide.

7. The assembly of claim 1, wherein the biasing element is a compression spring.

8. The assembly of claim 1, wherein the housing comprises an insert disposed in an outer cavity of the housing, the insert defining the cavity containing the inner race to be inserted through the opening of the housing, the insert defining an inner cavity.

9. The assembly of claim 8,
wherein the outer cavity defines a non-circular cross section parallel to the central axis, and
wherein an exterior of the insert is configured to interface with the outer cavity such that the insert is rotationally fixed in the outer cavity about the central axis.

10. The assembly of claim 1,
wherein the cavity comprises a plurality of grooves extending parallel to the central axis, and
wherein the interface of the inner race comprises a plurality of protrusions, each of the plurality of protrusions being translatably disposed in a corresponding one of the plurality of protrusions.

11. The assembly of claim 1,
wherein the housing defines a stop surface in the cavity positioned to be contacted by an end of an alignment guide such that the stop surface defines a position of maximum insertion of the alignment guide in the cavity, and
wherein the stop enables an impact force to be directed from the housing to an end of a fully inserted alignment guide via the stop.

12. The assembly of claim 1, wherein the housing defines a second opening into the cavity formed at the proximal end of the housing, the second opening being arranged such that an inner lumen of an alignment guide disposed in the central cavity of the inner race is accessible through the second opening.

13. The assembly of claim 1, wherein the outer race is rotationally fixed in the cavity about the central axis.

14. The assembly of claim 1, wherein the outer race is configured to abut the inner race when the inner race is biased distally to a fully extended position.

15. The assembly of claim 14, wherein, in the fully extended position, the plurality of clamping members are urged toward a maximally inward position with respect to the central axis.

16. The assembly of claim 14,
wherein the inner race is configured to abut the housing when the inner race is moved proximally to a fully compressed position, and
wherein, in the fully compressed position, the plurality of clamping elements are free to move to a maximally outward position with respect to the central axis.

17. The assembly of claim 1, comprising a handle coupled to the housing, the handle configured to enable a user to apply torque to the housing, the torque being transferred to an alignment guide disposed in the central passage via the interface of the inner race and the plurality of clamping elements.

18. The assembly of claim 1, further comprising:
a second opening to the cavity formed at the proximal end of the housing;
a second inner race disposed in the cavity of the housing and translatable in the cavity along the central axis, the second inner race comprising a second inner surface defining a second central passage concentrically aligned with the central passage and configured to receive the portion of an alignment guide after passing through the central passage of the inner race;
a second outer race disposed in the cavity and fixed along the central axis, the second outer race comprising a second inner surface surrounding a second outer surface of the second inner race, at least a portion of the second inner surface defining a second tapered region having decreasing diameter towards the second opening to the cavity, the decreasing diameter being with respect to the central axis;
a second plurality of clamping elements carried by the second inner race such that (i) movement of the second inner race proximally toward the second opening of the cavity engages the plurality of clamping elements against the second inner surface of the second outer race, the second inner surface urging the second plurality of clamping elements into the second central passage of the second inner race and towards the central axis, and (ii) movement of the second inner race distally away from the second opening of the cavity translates the second plurality of clamping elements along the second tapered region such that the increasing diameter allows the second plurality of clamping elements to move out of the second central passage and away from the central axis.

19. The assembly of claim 18, further comprising a second biasing element that urges the second inner race proximally along the central axis toward the second opening.

20. The assembly of claim 18, further comprising an end cap coupled to the second inner race and extending out of the second opening in the housing, the end cap defining a flange for applying a force to the second inner race in the distal direction to release an alignment guide.

21. The assembly of claim 1, further comprising an alignment guide, the alignment guide comprising a hollow shaft with a plurality of longitudinally-extending parallel grooves formed around an exterior portion of the hollow shaft, the hollow shaft being configured to be inserted into the central passage and the plurality of parallel grooves being configured to engage with the plurality of clamping elements.

22. The assembly of claim 21, wherein the plurality of parallel grooves are spaced such that a misaligned engagement of the exterior portion with the plurality of clamping elements results in the biased movement of the inner race rotating the alignment guide about the central axis such that the plurality of clamping elements are engaged in the plurality of parallel grooves.

23. The assembly of claim 1, wherein the plurality of clamping elements comprises ball bearings.

24. An assembly, comprising:
a housing having a cavity with an opening disposed at a distal end of the housing;
a first race disposed within the cavity and configured to translate relative to the housing along a longitudinal axis of the cavity extending from a proximal end thereof to the opening and remain locked against rotation relative to the housing about the longitudinal axis;
a plurality of bearing elements disposed within bores formed in the first race and configured to move radially relative to the longitudinal axis of the housing;
a second race disposed in the cavity of the housing and configured to remain fixed relative to the housing;
wherein the first race is biased distally toward the opening of the cavity;
wherein the second race surrounds the first race and includes an inner surface having a tapered diameter that decreases in a distal direction towards the opening;
wherein the inner surface of the second race is configured to contact the plurality of bearing elements as the first race moves distally relative to the second race such that inner surface of the second race urges the plurality of bearing elements radially inward.

25. The assembly of claim 24, wherein insertion of an alignment guide proximally into an opening in the first race causes the first race to translate proximally until the plurality of bearing elements move radially outward a sufficient amount to allow the alignment guide to pass further.

26. The assembly of claim 24,
wherein the first race is moveable in the proximal direction to an unclamped position where the plurality of bearing elements are allowed to move radially outward to permit insertion of an alignment guide proximally into an opening of the first race, and
wherein the first race is moveable in the distal direction to a clamped position wherein the plurality of bearing elements are urged radially inward to apply a clamping force to the alignment guide.

27. The assembly of claim 24, wherein, when an alignment guide is disposed such that the plurality of bearing elements prevent distal movement of the alignment guide, proximal translation of the first race enables distal movement of the alignment guide.

28. The assembly of claim 27, further comprising an end cap coupled to the first race, the end cap defining a flange for applying a force to the first race in the proximal direction to release an alignment guide.

29. The assembly of claim 24, wherein the housing defines a second opening into the cavity formed at the proximal end of the housing, the second opening being arranged such that an inner lumen of an alignment guide disposed in the housing is accessible through the second opening.

30. The assembly of claim 24, further comprising a handle coupled to the housing, the handle configured to enable a user to apply torque to the housing, the torque being transferred to an alignment guide disposed in the housing via the plurality of bearing elements.

31. The assembly of claim 24, further comprising:
a second opening to the cavity formed at the proximal end of the housing;
a third race disposed in the cavity of the housing and configured to translate relative to the housing along the longitudinal axis of the cavity and remain locked against rotation relative to the housing about the longitudinal axis;
a second plurality of bearing elements disposed within bores formed in the third race and configured to move radially relative to the longitudinal axis of the housing;
a fourth race disposed in the cavity of the housing and configured to remain fixed relative to the housing;
wherein the third race is biased proximally toward the second opening of the cavity;
wherein the fourth race surrounds the third race and includes an inner surface having a tapered diameter that decreases in a proximal direction towards the second opening;
wherein the inner surface of the fourth race is configured to contact the second plurality of bearing elements as the third race moves proximally relative to the fourth race such that the inner surface of the fourth race urges the second plurality of bearing elements radially inward.

32. The assembly of claim 31, further comprising an end cap coupled to the third race and extending out of the second opening in the housing, the end cap defining a flange for applying a force to the third race in the distal direction to release an alignment guide.

33. The assembly of claim 24, further comprising an alignment guide, the alignment guide comprising a hollow shaft with a plurality of longitudinally-extending parallel grooves formed around an exterior portion of the hollow shaft, the hollow shaft being configured to be inserted into the cavity of the housing and the plurality of parallel grooves being configured to engage with the plurality of bearing elements.

34. The bearing assembly of claim 33, wherein the plurality of parallel grooves are spaced such that a misaligned engagement of the exterior portion with the plurality of bearing elements results in the biased movement of the first race rotating the alignment guide about the longitudinal axis such that the plurality of bearing elements are engaged in the plurality of parallel grooves.

* * * * *